United States Patent
Martina et al.

(10) Patent No.: US 11,666,547 B2
(45) Date of Patent: Jun. 6, 2023

(54) METHODS FOR TREATING COGNITIVE DEFICITS IN A SUBJECT HAVING SCHIZOPHRENIA, BIPOLAR DISORDER, OR PSYCHIATRIC DEPRESSION, AND EXHIBITING COGNITIVE DEFICITS BY ADMINISTERING AN ANTAGONIST OF THE NA+-K+-2CL-CATION-CHLORIDE COTRANSPORTER ISOFORM 1 (NKCC1)

(71) Applicant: NORTHWESTERN UNIVERSITY, Evanston, IL (US)

(72) Inventors: Marco Martina, Evanston, IL (US); Herbert Y. Meltzer, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 56 days.

(21) Appl. No.: 16/915,746

(22) Filed: Jun. 29, 2020

(65) Prior Publication Data

US 2020/0405672 A1 Dec. 31, 2020

Related U.S. Application Data

(60) Provisional application No. 62/868,608, filed on Jun. 28, 2019.

(51) Int. Cl.
| | |
|---|---|
| *A61K 31/196* | (2006.01) |
| *A61K 31/4365* | (2006.01) |
| *A61P 25/18* | (2006.01) |
| *A61P 25/24* | (2006.01) |
| *A61K 31/57* | (2006.01) |
| *A61K 45/06* | (2006.01) |

(52) U.S. Cl.
CPC ........ *A61K 31/196* (2013.01); *A61K 31/4365* (2013.01); *A61K 31/57* (2013.01); *A61P 25/18* (2018.01); *A61P 25/24* (2018.01); *A61K 45/06* (2013.01)

(58) Field of Classification Search
CPC .... A61K 31/196; A61K 31/4365; A61P 25/18
See application file for complete search history.

(56) References Cited

U.S. PATENT DOCUMENTS

| | | |
|---|---|---|
| 10,098,893 B2 | 10/2018 | Li |
| 10,323,039 B2 | 6/2019 | Scheidt |
| 10,654,865 B2 | 5/2020 | Scheidt |
| 2015/0099741 A1 | 4/2015 | Li |
| 2016/0060702 A1 | 3/2016 | Li |
| 2019/0264285 A1 | 8/2019 | Li |

FOREIGN PATENT DOCUMENTS

WO WO-2007047698 A2 * 4/2007 ............. A61K 31/18

OTHER PUBLICATIONS

Mittleman et al., "The role of D1 and D2 receptors in the heightened locomotion induced by direct and indirect dopamine agonists in rats with hippocampal damage: an animal analogue of schizophrenia", Behavioural Brain Research, vol. 55, No. 2, pp. 253-267 (1993).*
Clark et al., "Chlorpromazine in Chronic Schizophrenia: Behavioral Dose-Response Relationships", Psychopharmacologia, vol. 18, No. 3, pp. 260-270 (1970).*
Wassef et al., "GABA and Schizophrenia: A Review of Basic Science and Clinical Studies", Journal of Clinical Psychopharmacology, vol. 23, No. 6, pp. 601-640 (2003).*
Aas et al. (2014) "A systematic review of cognitive function in first-episode psychosis, including a discussion on childhood trauma, stress, and inflammation." Front Psychiatry. Jan. 8, 2014;4:182.
Barbas et al (2016) "How the prefrontal executive got its stripes." Curr Opin Neurobiol. Oct. 2016;40:125-134.
Ben-Ari et al. (1989) "Giant synaptic potentials in immature rat CA3 hippocampal neurones." J Physiol. 1989;416:303-325.
Benes (1999) "Evidence for altered trisynaptic circuitry in schizophrenic hippocampus," Biol Psychiatry. Sep. 1, 1999;46(5):589-99. Review.
Cherubini et al. (1991) "GABA: an excitatory transmitter in early postnatal life." Trends Neurosci. Dec. 1991;14(12):515-9. Review.
Cohen et al. (2002) "On the origin of interictal activity in human temporal lobe epilepsy in vitro." Science. Nov. 15, 2002;298(5597):1418-21.
Deidda et al. (2015). "Reversing excitatory GABAAR signaling restores synaptic plasticity and memory in a mouse model of Down syndrome." Nat. Med. 21, 318-326 (2015).
Green et al. "Cognition in schizophrenia: Past, present, and future." Schizophrenia Research: Cognition 1.1 (2014):e1-e9.
Jentsch, J. D., et al. "The neuropsychopharmacology of phencyclidine: from NMDA receptor hypofunction to the dopamine hypothesis of schizophrenia." Neuropsychopharmacology 20.3 (1999): 201-225.
Kaneko et al "Cognitive remediation in schizophrenia." Clinical Psychopharmacology and Neuroscience 10.3 (2012): 125.
Kohli et al. (2019) "Oxytocin attenuates phencyclidine hyperactivity and increases social interaction and nucleus accumben dopamine release in rats." Neuropsychopharmacology. Jan. 2019;44(2):295-305.
Kool, M. J. et al. CAMK2-Dependent Signaling in Neurons is Essential for Survival, The Journal of neuroscience : the official journal of the Society for Neuroscience, 39 (2019) 5424-5439.

(Continued)

*Primary Examiner* — Kevin E Weddington
(74) *Attorney, Agent, or Firm* — Quarles & Brady LLP

(57) ABSTRACT

Disclosed are methods for treating a psychiatric disease or disorder and/or symptoms thereof in a subject in need thereof, the method comprising administering to the subject an effective amount of an antagonist of the Na+-K+-2Cl—cation-chloride cotransporter isoform 1 (NKCC1) for treating the psychiatric disorder and/or the symptoms thereof in the subject. The methods further may include administering to the subject a dopamine D1 agonist and/or a $GABA_A$ agonist, optionally at a subeffective dose, where co-administering the antagonist of NKCC1 improves the efficacy of the dopamine D1 agonist and/or the $GABA_A$ agonist, optionally at the subeffective dose, for treating the psychiatric disease or disorder and/or symptoms thereof.

26 Claims, 13 Drawing Sheets

(56) References Cited

OTHER PUBLICATIONS

Lepage et al. (2014) "Neurocognition: clinical and functional outcomes in schizophrenia." Can. J. Psychiatry. 2014;59(1):5-12.
Lewis et al. (1999) Altered GABA neurotransmission and prefrontal cortical dysfunction in schizophrenia. Biol Psychiatry. Sep. 1, 1999;46(5):616-26. Review.
Lewis et al. (2005) "Cortical inhibitory neurons and schizophrenia." Nat Rev Neurosci. Apr. 2005;6(4):312-24. Review.
McCarthy, S.E. et al. Microduplications of 16p11.2 are associated with schizophrenia, Nat Genet, 41 (2009) 1223-1227.
McLean et al. (2017) "Dopamine dysregulation in the prefrontal cortex relates to cognitive deficits in the sub-chronic PCP-model for schizophrenia: A preliminary investigation." J Psychopharmacol. Jun. 2017;31(6):660-666.
Niarchou, M. et al. Psychiatric disorders in children with 16p11.2 deletion and duplication, Translational psychiatry, 9 (2019) 8.
Papaleo, F. et al. Mouse models of genetic effects on cognition: relevance to schizophrenia, Neuropharmacology, 62(2012) 1204-1220.
Rannals et al. (2016) "Neurodevelopmental models of transcription factor 4 deficiency converge on a common ion channel as a potential therapeutic target for Pitt Hopkins syndrome." Rare Dis. Aug. 5, 2016;4(1):e1220468.
Steeds, H et al. "Drug models of schizophrenia." Therapeutic advances in psychopharmacology 5.1 (2015): 43-58.
Vertes (2006). "Interactions among the medial prefrontal cortex, hippocampus and midline thalamus in emotional and cognitive processing in the rat." Neuroscience. Sep. 29, 2006;142(1):1-20.
Völringer et al. (2013) "Cognitive impairment in bipolar disorder and schizophrenia: a systematic review." Frontiers in Psychiatry, 4, 87.
Yamasaki, N. et al. Alpha-CaMKII deficiency causes immature dentate gyrus, a novel candidate endophenotype of psychiatric disorders, Molecular brain, 1 (2008) 6.

* cited by examiner

METHODS FOR TREATING COGNITIVE DEFICITS IN A SUBJECT HAVING SCHIZOPHRENIA, BIPOLAR DISORDER, OR PSYCHIATRIC DEPRESSION, AND EXHIBITING COGNITIVE DEFICITS BY ADMINISTERING AN ANTAGONIST OF THE NA+-K+-2CL-CATION-CHLORIDE COTRANSPORTER ISOFORM 1 (NKCC1)

CROSS-REFERENCE TO RELATED PATENT APPLICATIONS

The present application claims the benefit of priority under 35 U.S.C. § 119(e) to U.S. Provisional Application No. 62/868,608, filed on Jun. 28, 2019, the content of which is incorporated herein by reference in its entirety.

STATEMENT REGARDING FEDERALLY SPONSORED RESEARCH OR DEVELOPMENT

This invention was made with government support under DA044121 and NS064091 awarded by the National Institutes of Health. The government has certain rights in the invention.

BACKGROUND

The invention relates to methods and compositions for treating psychiatric disorders and the symptoms thereof. In particular, the intention relates to methods for treating psychiatric disorders and the symptoms thereof, such as schizophrenia and cognitive symptoms thereof by administering an antagonist of the Na+-K+-2Cl— cation-chloride cotransporter isoform 1 (NKCC1), such as bumetanide, either alone as a therapeutic agent or by additionally administering a dopamine D1 agonist, a dopamine D1/D2 antagonist, and/or a gamma-aminobutyric acid A receptor ($GABA_A$) agonist.

Cognitive deficits are the components of the schizophrenia syndrome that contribute the most to the poor functional outcome and low quality of life of schizophrenic patients, although both positive symptoms and negative symptoms, the other key features of this syndrome, may be greater contributors to the toll this illness takes on patients. While current pharmacological treatments with antipsychotics have beneficial effects on the positive symptoms (delusions and hallucinations) of schizophrenia in about 70-90% of patients, they have lesser effect on negative and cognitive symptoms, making the need for better treatments an urgent priority.

Here, the inventors show that oral administration of bumetanide, an antagonist of the NKCC1 cation-chloride cotransporter and an FDA-approved diuretic drug, is effective to prevent and treat the cognitive deficits as well as the negative and positive symptoms associated with schizophrenia. Treatment with bumetanide should lead to improved overall function for schizophrenia patients and less frequent or briefer relapses and hospitalization, thus, achieving considerable reductions in the cost of treating schizophrenia.

The inventors also have found that bumetanide may be administered alone or together with other therapeutic agents for treating psychiatric disorders, which may provide synergistic action in treating the psychiatric disorders. For example, a subeffective dose of a dopamine D1 agonist, a dopamine D1/D2 antagonist, and/or a subeffective dose of $GABA_A$ agonist may be administered together with bumetamide to treat psychiatric disorders.

The inventors' findings may lead to repurposing of NKCC1 antagonists such as bumetanide, for treating psychiatric disorders. The inventors' findings also may lead to new formulations and/or combination therapies for treating psychiatric disorders that use NKCC1 antagonists such as bumetanide, and that use subeffective doses of dopamine D1 agonists, dopamine D1/D2 antagonists, $GABA_A$ agonists, and/or neurosteroids, which subeffective doses may be effective when administered with the NKCC1 antagonist thereby minimizing the likelihood of undesired side effects of higher doses.

SUMMARY

Disclosed are methods and compositions for treating a psychiatric disease or disorder and/or symptoms thereof in a subject in need thereof, the method comprising administering to the subject an effective amount of an antagonist of the Na+-K+-2Cl— cation-chloride cotransporter isoform 1 (NKCC1) for treating the psychiatric disorder and/or the symptoms thereof in the subject. The methods further may include administering to the subject a dopamine D1 agonist, a dopamine D1/D2 antagonist, and/or a $GABA_A$ agonist, optionally at an otherwise subeffective dose, where co-administering the antagonist of NKCC1 improves the efficacy of the dopamine D1 agonist, the dopamine D1/D2 antagonist, and/or the $GABA_A$ agonist for treating the psychiatric disease or disorder and/or symptoms thereof at the otherwise subeffective dose. Suitable antagonists of NKCC1 may include, but are not limited to, bumetanide.

Psychiatric diseases and disorders treated by the disclosed methods and compositions may include, but are not limited to schizophrenia, bipolar disorder, and psychiatric depression. Symptoms of psychiatric diseases and disorders treated by the disclosed methods may include one or more of positive symptoms, negative symptoms, cognitive symptoms, and any combination thereof.

DETAILED DESCRIPTION

Figure 1:
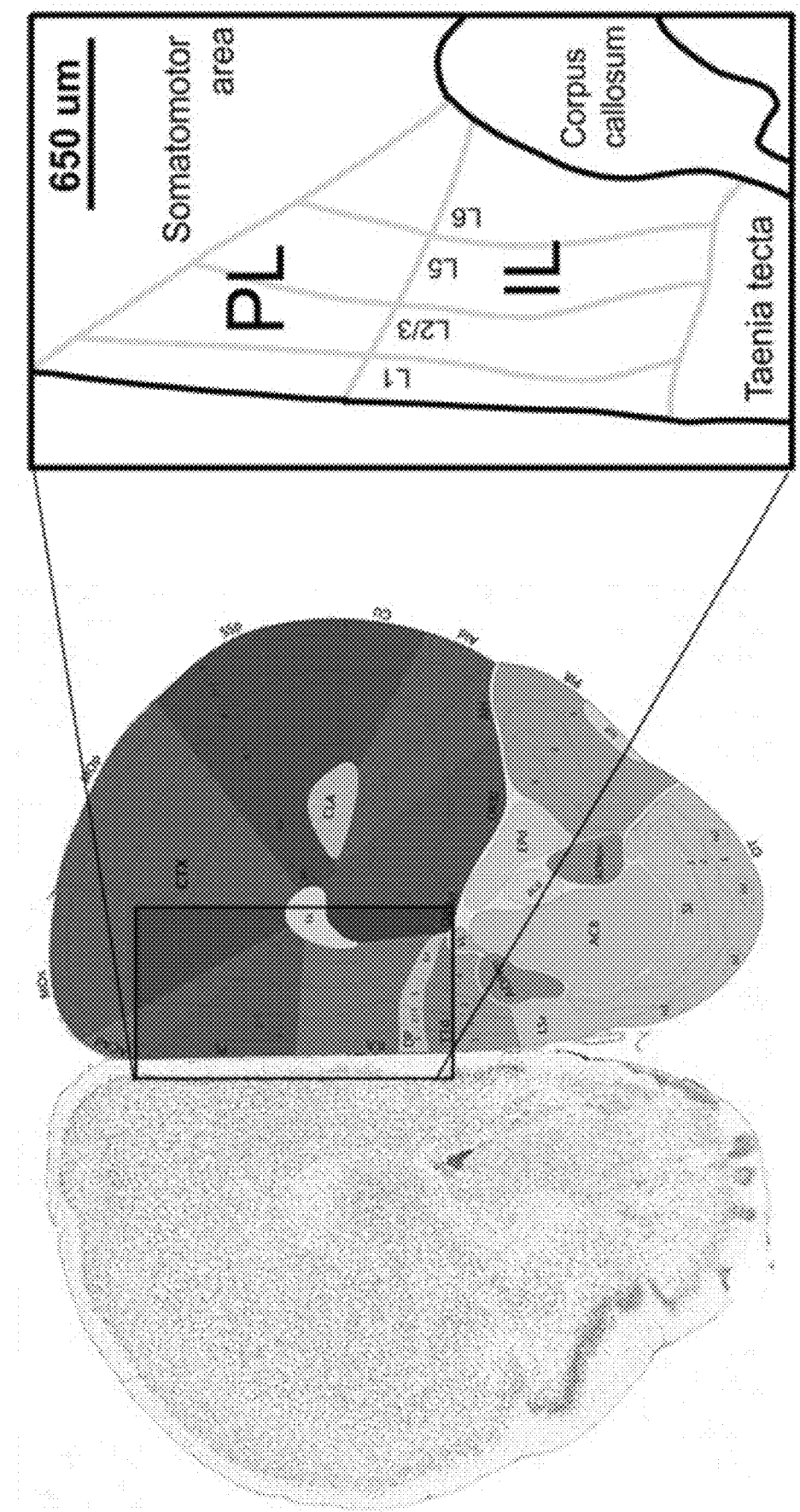
FIG. 1. Subdivisions of the medial prefrontal cortex (mPFC).

Disclosed are methods and compositions for treating psychiatric diseases and disorders and the symptoms thereof. The methods and compositions are described herein using several definitions, as set forth below and throughout the application.

As used in this specification and the claims, the singular forms "a," "an," and "the" include plural forms unless the context clearly dictates otherwise. For example, "a therapeutic agent" should be interpreted to mean "one or more therapeutic agents" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The presently disclosed methods and compositions relate to therapeutic treatment of subjects in need thereof. As used herein, the term "subject," which may be used interchangeably with the terms "patient" or "individual," refers to one who receives medical care, attention or treatment and may encompass a human patient. As used herein, the term "patient" is meant to encompass a person who has a psychiatric disorder or is at risk for developing a psychiatric disorder, which includes but is not limited to schizophrenia, bipolar disorder, and psychotic depression (e.g., depression with psychotic features). For example, the term "subject" is meant to encompass a person at risk for developing schizophrenia or a person diagnosed with schizophrenia (e.g., a person who may be symptomatic for schizophrenia but who has not yet been diagnosed). As used herein, "schizophrenia" may include schizophrenia characterized by positive symptoms, negative symptoms, cognitive symptoms, or any combination thereof. The term "subject" also is meant to encompass a person at risk for developing bipolar disorder or a person diagnosed with bipolar disorder (e.g., a person who may be symptomatic for bipolar disorder but who has not yet been diagnosed). The term "subject" further is meant to encompass a person at risk for developing depression (e.g., depression with psychotic features). As such, the term "subject" further is meant to encompass a person at risk for developing depression with psychotic features or a person diagnosed with depression with psychotic features (e.g., a person who may be symptomatic for depression with psychotic features but who has not yet been diagnosed).

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

As used herein, the term "modulate" means decreasing or inhibiting activity and/or increasing or augmenting activity. Modulating NKCC1 activity may mean decreasing or inhibiting NKCC1 activity. The compounds disclosed herein may be administered to modulate NKCC1 activity, for example, to decrease NKCC1 activity as an antagonist of NKCC1. Modulating dopamine D1 receptor activity and/or $GABA_A$ receptor activity may mean increasing or augmenting dopamine D1 receptor activity and/or $GABA_A$ receptor activity. The compounds disclosed herein may be administered to modulate dopamine D1 receptor activity and/or $GABA_A$ receptor activity, for example, in increase dopamine D1 receptor activity and/or $GABA_A$ receptor activity as agonists of the dopamine D1 receptor and/or the $GABA_A$ receptor, or to decrease dopamine D1/D2 receptor activity as antagonists of the dopamine D1, D2, D3, D4, D5 receptors.

The compounds utilized in the treatment methods disclosed herein may exhibit one or more biological activities. The disclosed compounds may function as antagonist of NKCC1. In some embodiments, the disclosed compounds inhibit the activity of NKCC1 by at least 50%, 60%, 70%, 80%, 90%, 95%, 96%, 97%, 98%, or 99% at a concentration of less than about 100 µM, 50 µM, 10 µM, 1 µM, 0.1 µM, 0.05 µM, 0.01 µM, 0.005 µM, 0.001 µM, or less. The disclosed compounds may function as agonists for the dopamine D1 receptor and/or the $GABA_A$ receptor. The disclosed compounds may function as antagonists for the dopamine D1/D2 receptors (i.e., the D1, D2, D3, D4, or D5 receptor).

The disclosed compounds may be formulated as therapeutics for treating psychiatric diseases and disorders and/or the symptoms thereof. The disclosed compounds may be formulated for treating schizophrenia, bi-polar disorder, and/or psychiatric depression. The disclosed compounds may be formulated for treating symptoms of psychiatric diseases and disorders, such as positive symptoms, negative symptoms, cognitive symptoms, and combinations thereof.

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 µM, 0.005 µM, 0.01 µM, 0.5 µM, 0.1 µM, 1.0 µM, 10 µM, and 100 µM (e.g., 0.1 µM-1.0 µM).

In some embodiments of the disclosed treatment methods, the subject may be administered a dose of a compound as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds may include doses falling within dose ranges having as end-points any of these disclosed doses (e.g., 2.5 mg-200 mg).

In some embodiments, a minimal dose level of a compound for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a compound for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the compounds for achieving therapy in the disclosed methods of treatment may include dose levels falling within ranges having as end-points any of these disclosed dose levels (e.g., 500-2000 ng/kg body weight of the subject).

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The disclosed compounds or pharmaceutical compositions comprising the disclosed compounds may be administered in methods of treatment. For example, the disclosed compounds or pharmaceutical compositions comprising the disclosed compounds may be administered in methods of treating psychiatric diseases and disorders and/or the symptoms thereof.

Optionally, the disclosed compounds or pharmaceutical compositions comprising the disclosed compounds may be administered with additional therapeutic agents, optionally in combination, in order to treat psychiatric diseases and disorders. In some embodiments of the disclosed methods, one or more additional therapeutic agents are administered with the disclosed compounds or with pharmaceutical compositions comprising the disclosed compounds, where the additional therapeutic agent is administered prior to, concurrently with, or after administering the disclosed compounds or the pharmaceutical compositions comprising the disclosed compounds. In some embodiments, the disclosed pharmaceutical composition are formulated to comprise the disclosed compounds and further to comprise one or more additional therapeutic agents, for example, one or more additional therapeutic agents for treating psychiatric diseases and disorders.

Methods for Treating Psychiatric Diseases and Disorders and the Symptoms thereof in a Subject by Administering an Antagonist of the Na+-K+-2Cl— Cation-Chloride Cotransporter Isoform 1 (NKCC1)

Disclosed are methods and compositions for treating a psychiatric disease or disorder and/or symptoms thereof in a subject in need thereof. The disclosed methods typically include administering to the subject an effective amount of an antagonist of the Na+-K+-2Cl— cation-chloride cotransporter isoform 1 (NKCC1) for treating the psychiatric disorder and/or the symptoms thereof in the subject.

In some embodiments of the disclosed methods, the subject has a psychiatric disease or disorder selected from the group consisting of schizophrenia, bipolar disorder, and psychiatric depression, which psychiatric disease is treated by the treatment method. In some embodiments of the disclosed methods, the subject has a symptom of a psychiatric disorder selected from positive symptoms, negative symptoms, cognitive symptoms, and any combination thereof, which symptom is treated by the treatment method.

In the disclosed methods, the subject is administered an antagonist of NKCC1. In some embodiments, the antagonist of NKCC1 is selected from the group consisting of bumetanide, furosemide, piretanide, benzmetanide, azosemide, torasemide (torsemide), tripamide, and tizolemide.

Preferably, the antagonist of NKCC1 is bumetanide or a pharmaceutical salt thereof. Bumetanide has the formula:

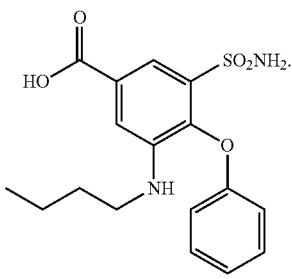 [SMILES: CCCCNc1cc(C(=O)O)cc(S(N)(=O)=O)c1Oc1ccccc1]

In the disclosed methods, the subject may be administered an additional therapeutic agent for treating a psychiatric disease or disorder or symptoms thereof. The additional therapeutic agent may be administered before, concurrently with, or after the antagonist of NKCC1.

In some embodiments of the disclosed methods, the subject is administered an agonist of the dopamine D1 receptor in addition to the antagonist of NKCC1, optionally where the agonist of the dopamine D1 receptor is administered at a subeffective dose when the agonist of the dopamine D1 receptor is administered without the antagonist of NKCC1. Suitable agonists of the dopamine D1 receptor may include, but are not limited to, A-86929, dihydrexidine, dinapsoline, dinoxyline, doxanthrine, SKF-81297, SKF-82958, SKF-38393, fenoldopam, 6-Br-APB, stepholidine, A-68930, A-77636, CY-208,243, SKF-89145, SKF-89626, 7,8-dihydroxy-5-phenyl-octahydrobenzo[h]isoquinoline, cabergoline, and pergolide. In some embodiments, the subject is administered SKF-38393 in addition to an antagonist of NKCC1, such as bumetanide.

In some embodiments of the disclosed methods, the subject is administered an antagonist of the dopamine D1/D2 receptor in addition to the antagonist of NKCC1, optionally where the antagonist of the dopamine D1/D2 receptor is administered at a subeffective dose when the antagonist of the dopamine D1/D2 receptor is administered without the antagonist of NKCC1. Suitable antagonists of the dopamine D1 receptor may include, but are not limited to, benperidol, chlorpromazine, clopenthixol, droperidol, haloperidol, fluphenazine, flupenthixol, flupirilene, penfluridol, perazine, perphenazine, pimozide, spiperone, sulpiride, thioridazine, amisulphride, asenapine, aripiprazole, clozapine, loxapine, nemonapride, olanzapine, quetiapine, paliperidone, remoxipride, risperidone, tiapride, and ziprasidone. In some embodiments, the subject is administered risperidone in addition to an antagonist of NKCC1, such as bumetanide.

In other embodiments of the disclosed methods, the subject is administered an agonist of the $GABA_A$ receptor in addition to the antagonist of NKCC1, optionally where the agonist of the $GABA_A$ receptor is administered at a subeffective dose when the agonist of the $GABA_A$ receptor is administered without the antagonist of NKCC1. Suitable agonists of the $GABA_A$ receptor may include, but are not limited to, ADX-71441, alcohols, avermectins (e.g., ivermectin), babamide, baclofen, barbiturates (e.g., phenobarbital), bamaluzole, benzodiazepines (e.g., diazepam, alprazolam), bromides (e.g., potassium bromide), 1,4-butanediol, carbamates (e.g., meprobamate, carisoprodol), chloralose, chlormezanone, clomethiazole, dihydroergolines (e.g., ergoloid (dihydroergotoxine)), etazepine, etifoxine, GABA, gabamide, GABOB, gaboxadol, gamma-butyrolactone (GBL), gamma-hydroxybutyric acid (GHB), gamma-hydroxyvaleric acid (GHV), gamma-valerolactone (GVL), ibotenic acid, imidazoles (e.g., etomidate), isoguvacine, isonipecotic acid, kavalactones, lesogaberan, loreclezole, muscimol, neuroactive steroids (e.g., allopregnanolone, ganaxolone), non-benzodiazepines (e.g., zaleplon, zolpidem, zopiclone, eszopiclone), petrichloral, phenibut, picamilon, piperidinediones (e.g., glutethimide, methyprylon), progabide, propanidid, propofol, pyrazolopyridines (e.g., etazolate), quinazolinones (e.g., methaqualone), quisqualamine, SL-75102, stiripentol, sulfonylalkanes (e.g., sulfonmethane, tetronal, trional), thiomuscimol, tolgabide, valerian constituents (e.g., valeric acid, valerenic acid), volatiles/gases (e.g., chloral hydrate, chloroform, diethyl ether, sevoflurane), and zolpidem. In some embodiments, the subject is administered gaboxadol in addition to an antagonist of NKCC1, such as bumetanide. In other embodiments, the subject is administered allopregnanolone in addition to an antagonist of NKCC1, such as bumetanide.

Also disclosed are pharmaceutical kits, which optionally may be utilized in methods for treating a psychiatric disorder or disease or symptoms thereof. In some embodiments, the pharmaceutic kit comprises as components: (i) an antagonist of the Na+-K+-2Cl— cation-chloride cotransporter isoform 1 (NKCC1); and (ii) an agonist of the dopamine D1 receptor, optionally where the kit comprises a dose of the agonist of the dopamine D1 receptor which is a subeffective dose for treating a psychiatric disorder when the agonist of the dopamine D1 receptor is administered without the antagonist of NKCC1. In some embodiments, the pharmaceutic kit comprises as components: (i) an antagonist of the Na+-K+-2Cl— cation-chloride cotransporter isoform 1 (NKCC1); and (ii) an antagonist of the dopamine D1/DS2 receptor, optionally where the kit comprises a dose of the antagonist of the dopamine D1/D2 receptor which is a subeffective dose for treating a psychiatric disorder when the antagonist of the dopamine D1/D2 receptor is administered without the antagonist of NKCC1. In some embodiments, the pharmaceutic kit comprises as components: (i) an antagonist of the Na+-K+-2Cl— cation-chloride cotransporter isoform 1 (NKCC1); and (ii) an agonist of the the $GABA_A$ receptor, optionally where the kit comprises a dose of the agonist of the $GABA_A$ receptor which is a subeffective dose for treating a psychiatric disorder when the agonist of the $GABA_A$ receptor is administered without the antagonist of NKCC1. Component (i) and component (ii) may be formulated as separate dosage forms in the kit (e.g., where component (i) is administered before or after component (ii)) and/or component (i) and component (ii) may be formulated together in a single dosage form (e.g., where component (i) and component (ii) are administered concurrently).

ILLUSTRATED EMBODIMENTS

The following Embodiments are illustrative and should not be interpreted to limit the claimed subject matter Embodiment 1. A method for treating a psychiatric disease or disorder and/or symptoms thereof in a subject in need thereof, the method comprising administering to the subject an effective amount of an antagonist of the Na+-K+-2Cl— cation-chloride cotransporter isoform 1 (NKCC1) for treating the psychiatric disorder and/or the symptoms thereof in the subject.

Embodiment 2. The method of embodiment 1, wherein the subject has a psychiatric disease or disorder selected from the group consisting of schizophrenia, bipolar disorder, and psychiatric depression.

Embodiment 3. The method of embodiment 1 or embodiment 2, wherein the subject is exhibiting symptoms selected from the group consisting of positive symptoms, negative symptoms, cognitive symptoms, and any combination thereof.

Embodiment 4. The method of any of the foregoing embodiments, wherein the antagonist of NKCC1 is selected from the group consisting of bumetanide, furosemide, piretanide, benzmetanide, azosemide, torasemide (torsemide), tripamide, and tizolemide.

Embodiment 5. The method of any of the foregoing embodiments, wherein the antagonist of NKCC1 is bumetanide.

Embodiment 6. The method of any of the foregoing embodiments, further comprising administering to the subject an agonist of the dopamine D1 receptor, wherein the agonist of the dopamine D1 receptor is administered before, concurrently with, or after the antagonist of NKCC1, optionally wherein the agonist of the dopamine D1 receptor is administered at a dose which is a subeffective dose when the agonist of the dopamine D1 receptor is administered without the antagonist of NKCC1.

Embodiment 7. The method of embodiment 5, wherein the agonist of the dopamine D1 receptor is selected from A-86929, dihydrexidine, dinapsoline, dinoxyline, doxanthrine, SKF-81297, SKF-82958, SKF-38393, fenoldopam, 6-Br-APB, stepholidine, A-68930, A-77636, CY-208,243, SKF-89145, SKF-89626, 7,8-dihydroxy-5-phenyl-octahydrobenzo[h]isoquinoline, cabergoline, and pergolide.

Embodiment 8. The method of embodiment 6 or 7, wherein the agonist of the dopamine D1 receptor is SKF-38393.

Embodiment 9. The method of any of the foregoing embodiments, further comprising administering to the subject an antagonist of the dopamine D1/D2 receptor, wherein the antagonist of the dopamine D1/D2 receptor is administered before, concurrently with, or after the antagonist of NKCC1, optionally wherein the antagonist of the dopamine D1/D2 receptor is administered at a dose which is a subeffective dose when the antagonist of the dopamine D1/D2 receptor is administered without the antagonist of NKCC1.

Embodiment 10. The method of embodiment 9, wherein the antagonist of the dopamine D1/D2 receptor is selected from benperidol, chlorpromazine, clopenthixol, droperidol, haloperidol, fluphenazine, flupenthixol, flupirilene, penfluridol, perazine, perphenazine, pimozide, spiperone, sulpiride, thioridazine, amisulphride, asenapine, aripiprazole, clozapine, loxapine, nemonapride, olanzapine, quetiapine, paliperidone, remoxipride, risperidone, tiapride, and ziprasidone.

Embodiment 11. The method of embodiment 9 or 10, wherein the antagonist of the dopamine D1/D2 receptor is risperidone.

Embodiment 12. The method of any of the foregoing embodiments, further comprising administering to the subject an agonist of the $GABA_A$ receptor, wherein the agonist of the $GABA_A$ receptor is administered before, concurrently with, or after the antagonist of NKCC1, optionally wherein the agonist of the $GABA_A$ receptor is administered at a dose which is a subeffective dose when the agonist of the $GABA_A$ receptor is administered without the antagonist of NKCC1.

Embodiment 13. The method of embodiment 12, wherein the agonist of the $GABA_A$ receptor is selected from the group consisting of ADX-71441, alcohols, avermectins (e.g., ivermectin), babamide, baclofen, barbiturates (e.g., phenobarbital), bamaluzole, benzodiazepines (e.g., diazepam, alprazolam), bromides (e.g., potassium bromide), 1,4-butanediol, carbamates (e.g., meprobamate, carisoprodol), chloralose, chlormezanone, clomethiazole, dihydroergolines (e.g., ergoloid (dihydroergotoxine)), etazepine, etifoxine, GABA, gabamide, GABOB, gaboxadol, gamma-butyrolactone (GBL), gamma-hydroxybutyric acid (GHB), gamma-hydroxyvaleric acid (GHV), gamma-valerolactone (GVL), ibotenic acid, imidazoles (e.g., etomidate), isoguvacine, isonipecotic acid, kavalactones, lesogaberan, loreclezole, muscimol, neuroactive steroids (e.g., allopregnanolone, ganaxolone), non-benzodiazepines (e.g., zaleplon, zolpidem, zopiclone, eszopiclone), petrichloral, phenibut, picamilon, piperidinediones (e.g., glutethimide, methyprylon), progabide, propanidid, propofol, pyrazolopyridines (e.g., etazolate), quinazolinones (e.g., methaqualone), quisqualamine, SL-75102, stiripentol, sulfonylalkanes (e.g., sulfonmethane, tetronal, trional), thiomuscimol, tolgabide, valerian constituents (e.g., valeric acid, valerenic acid), volatiles/gases (e.g., chloral hydrate, chloroform, diethyl ether, sevoflurane), and zolpidem.

Embodiment 14. The method of embodiment 12 or 13, wherein the agonist of the $GABA_A$ receptor is gaboxadol.

Embodiment 15. The method of embodiment 12 or 13, wherein the agonist of the $GABA_A$ receptor is allopregnanolone.

Embodiment 16. A pharmaceutical kit comprising as components: (i) an antagonist of the Na+-K+-2Cl— cation-chloride cotransporter isoform 1 (NKCC1); and (ii) an agonist of the dopamine D1 receptor, optionally wherein the kit comprises a dose of the agonist of the dopamine D1 receptor which is a subeffective dose for treating a psychiatric disorder when the agonist of the dopamine D1 receptor is administered without the antagonist of NKCC1.

Embodiment 17. The pharmaceutical kit of embodiment 16, wherein the antagonist of NKCC1 is selected from the group consisting of bumetanide, furosemide, piretanide, benzmetanide, azosemide, torasemide (torsemide), tripamide, and tizolemide.

Embodiment 18. The pharmaceutical kit of embodiment 16 or 17, wherein the antagonist of NKCC1 is bumetanide.

Embodiment 19. The pharmaceutical kit of any of embodiments 16-18, wherein the agonist of the dopamine D1 receptor is selected from A-86929, dihydrexidine, dinapsoline, dinoxyline, doxanthrine, SKF-81297, SKF-82958, SKF-38393, fenoldopam, 6-Br-APB, stepholidine, A-68930, A-77636, CY-208,243, SKF-89145, SKF-89626, 7,8-dihydroxy-5-phenyl-octahydrobenzo[h]isoquinoline, cabergoline, and pergolide.

Embodiment 20. The pharmaceutical kit of any of embodiments 16-19, wherein the agonist of the dopamine D1 receptor is SKF-38393.

Embodiment 21. The pharmaceutical kit of any of embodiments 16-20, wherein component (i) and component (ii) are formulated as separate dosage forms in the kit.

Embodiment 22. The pharmaceutical kit of any of embodiments 16-20, wherein component (i) and component (ii) are formulated as a single dosage form in the kit.

Embodiment 23. A pharmaceutical kit comprising as components: (i) an antagonist of the Na+-K+-2Cl— cation-chloride cotransporter isoform 1 (NKCC1); and (ii) an antgonist of the dopamine D1/D2 receptor, optionally wherein the kit comprises a dose of the antagonist of the dopamine D1/D2 receptor which is a subeffective dose for treating a psychiatric disorder when the antagonist of the dopamine D1/D2 receptor is administered without the antagonist of NKCC1.

Embodiment 24. The pharmaceutical kit of embodiment 23, wherein the antagonist of NKCC1 is selected from the group consisting of bumetanide, furosemide, piretanide, benzmetanide, azosemide, torasemide (torsemide), tripamide, and tizolemide.

Embodiment 25. The pharmaceutical kit of embodiment 23 or 24, wherein the antagonist of NKCC1 is bumetanide.

Embodiment 26. The pharmaceutical kit of any of embodiments 23-25, wherein the antagonist of the dopamine D1/D2 receptor is selected from benperidol, chlorpromazine, clopenthixol, droperidol, haloperidol, fluphenazine, flupenthixol, flupirilene, penfluridol, perazine, perphenazine, pimozide, spiperone, sulpiride, thioridazine, amisulphride, asenapine, aripiprazole, clozapine, loxapine, nemonapride, olanzapine, quetiapine, paliperidone, remoxipride, risperidone, tiapride, and ziprasidone.

Embodiment 27. The pharmaceutical kit of any of embodiments 23-26, wherein the antgonist of the dopamine D1/D2 receptor is risperidone.

Embodiment 28. The pharmaceutical kit of any of embodiments 23-27, wherein component (i) and component (ii) are formulated as separate dosage forms in the kit.

Embodiment 29. The pharmaceutical kit of any of embodiments 23-27, wherein component (i) and component (ii) are formulated as a single dosage form in the kit.

Embodiment 30. A pharmaceutical kit comprising as components: (i) an antagonist of the Na+-K+-2Cl— cation-chloride cotransporter isoform 1 (NKCC1); and (ii) an agonist of the $GABA_A$ receptor, optionally wherein the kit comprises a dose of the agonist of the $GABA_A$ receptor which is a subeffective dose for treating a psychiatric disorder when the agonist of the $GABA_A$ receptor is administered without the antagonist of NKCC1.

Embodiment 31. The pharmaceutical kit of embodiment 30, wherein the antagonist of NKCC1 is selected from the group consisting of bumetanide, furosemide, piretanide, benzmetanide, azosemide, torasemide (torsemide), tripamide, and tizolemide.

Embodiment 32. The pharmaceutical kit of embodiment 30 or 31, wherein the antagonist of NKCC1 is bumetanide.

Embodiment 33. The pharmaceutical kit of any of embodiments 30-32, wherein the agonist of the $GABA_A$ receptor is selected from the group consisting of ADX-71441, alcohols, avermectins (e.g., ivermectin), babamide, baclofen, barbiturates (e.g., phenobarbital), bamaluzole, benzodiazepines (e.g., diazepam, alprazolam), bromides (e.g., potassium bromide), 1,4-butanediol, carbamates (e.g., meprobamate, carisoprodol), chloralose, chlormezanone, clomethiazole, dihydroergolines (e.g., ergoloid (dihydroergotoxine)), etazepine, etifoxine, GABA, gabamide, GABOB, gaboxadol, gamma-butyrolactone (GBL), gamma-hydroxybutyric acid (GHB), gamma-hydroxyvaleric acid (GHV), gamma-valerolactone (GVL), ibotenic acid, imidazoles (e.g., etomidate), isoguvacine, isonipecotic acid, kavalactones, lesogaberan, loreclezole, muscimol, neuroactive steroids (e.g., allopregnanolone, ganaxolone), non-benzodiazepines (e.g., zaleplon, zolpidem, zopiclone, eszopiclone), petrichloral, phenibut, picamilon, piperidinediones (e.g., glutethimide, methyprylon), progabide, propanidid, propofol, pyrazolopyridines (e.g., etazolate), quinazolinones (e.g., methaqualone), quisqualamine, SL-75102, stiripentol, sulfonylalkanes (e.g., sulfonmethane, tetronal, trional), thiomuscimol, tolgabide, valerian constituents (e.g., valeric acid, valerenic acid), volatiles/gases (e.g., chloral hydrate, chloroform, diethyl ether, sevoflurane), and zolpidem.

Embodiment 34. The pharmaceutical kit of any of embodiments 30-33, wherein the agonist of the $GABA_A$ receptor is gaboxadol.

Embodiment 35. The pharmaceutical kit of any of embodiments 30-33, wherein the agonist of the $GABA_A$ receptor is allopregnanolone.

Embodiment 36. The pharmaceutical kit of any of embodiments 30-35, wherein component (i) and component (ii) are formulated as separate dosage forms in the kit.

Embodiment 37. The pharmaceutical kit of any of embodiments 30-35, wherein component (i) and component (ii) are formulated as a single dosage form in the kit.

Examples

The following Examples are illustrative and should not be interpreted to limit the claimed subject matter.

Depolarizing $GABA_A$ currents in the prelimbic cortex mediate cognitive impairment in a mouse model of schizophrenia and are modulated by the NKCC1 antagonist, bumetanide.

Abstract

We found that in the sub-chronic phencyclidine (PCP) model of the negative and cognitive symptoms of schizophrenia the reversal of the $GABA_A$-receptor mediated current is strongly shifted toward depolarized potential in pyramidal neurons of the infralimbic cortex, and thus activation of $GABA_A$ receptors becomes excitatory. Excitatory $GABA_A$ current is well-known to exist in the neonatal brain (Ben-Ari et al. 1989), and has more recently been shown to have a pathogenic role in the cognitive effects of Down syndrome (Deidda et al. 2015).

Bumetanide acts by blocking the NKCC1 cation-chloride cotransporter and causes the reversal potential of the $GABA_A$-mediated current to become more hyperpolarized (thus the inhibitory effect becomes stronger). We found that pharmacological inhibition of chloride transport with bumetanide normalizes the $GABA_A$-mediated current reversal potential ex-vivo (in acute slices of the IL cortex). Most importantly, in-vivo administration of bumetanide rescues cognitive function in PCP mice and also prevents enduring deficit of cognitive function. Bumetanide (0.1 mg/kg) significantly rescued memory deficit in scPCP-treated mice subjected to chronic unpredictable stress (CUS; 21 days), a model of cognitive dysfunction in treatment-resistant schizophrenia, major depression, bipolar disorder, and post-traumatic stress disorder.

Introduction

Cognitive deficits are critical predictors of the clinical and social outcomes in schizophrenic patients (Lepage et al. 2014). Unfortunately, while current pharmacological treatments with antipsychotics have beneficial effects on the positive symptoms of schizophrenia, they lack efficacy against the negative and cognitive symptoms (Kaneko and Keshavan 2012; Green 2016). The prefrontal cortex (PFC) is a brain area critically involved in executive planning and memory functions (Barbas and Garcia-Cabezas 2016), which are both compromised in schizophrenia (Aas et al. 2014; Vöhringer et al. 2013). Yet, how PFC networks are affected in schizophrenia remains unclear. In particular, there is a longstanding debate concerning the fate of GABAergic interneurons in the schizophrenic brain and the potential role of altered GABAergic inhibition in the PFC of schizophrenic patients (Benes 1999; Lewis et al. 1999; Lewis et al. 2005). The conflicting results may, at least in part, be the consequence of the fact that the PFC is composed of two main sub-regions, the prelimbic cortex (PLC) and the infralimbic cortex (ILC). While the rodent ILC/PLC functions as a whole to control emotional and cognitive aspects of goal-directed behavior, the two areas have different connectivity and functions (Vertes 2006). Yet, most rodent studies do not differentiate between the two regions (Rannals et al. 2016; McLean et al. 2017; Kohli et al. 2019). An additional potential complication is that the functional effect of $GABA_A$ currents depends on the concentration of intracellular chloride, which is regulated by the expression ratio in the postsynaptic neurons of the chloride/potassium co-transporters NKCC1 and KCC2. The activity ratio of these transporters sets the reversal potential of the $GABA_A$ current and is dynamically regulated. Excitatory $GABA_A$ current was first described in the neonatal brain (Ben-Ari et al. 1989). $GABA_A$ current is depolarizing in early developmental stages (reviewed by Cherubini et al. 1991) as well as in adulthood in some pathological conditions such as epilepsy and Down syndrome (Cohen et al. 2002, Deidda et al. 2015). The cellular mechanisms that mediate the cognitive and negative deficits in schizophrenia remain largely unknown. While the nature of these deficits implicate the prefrontal cortex, little information is available.

Experiments and Results

Figure 2:
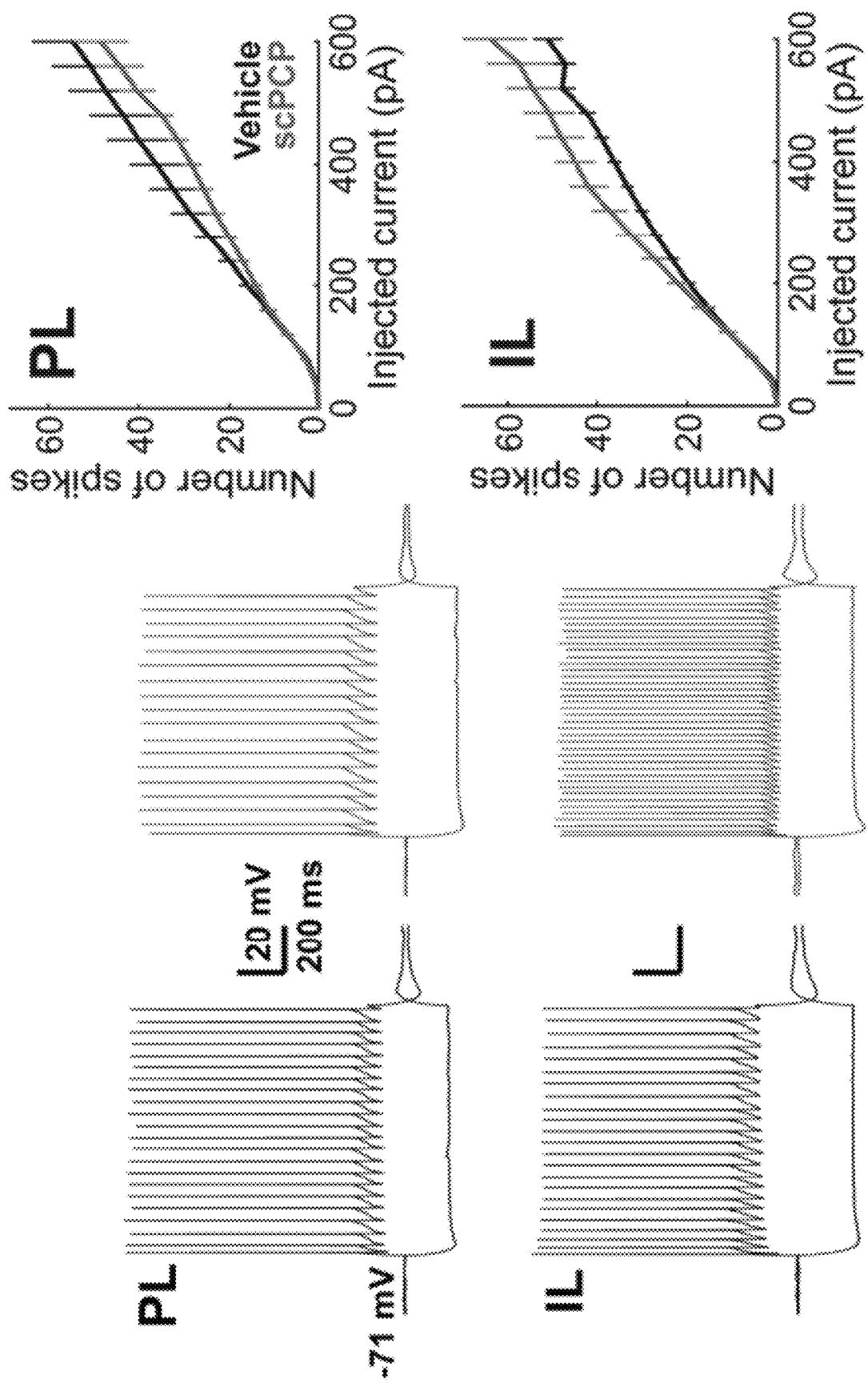
FIG. 2. scPCP treatment causes increased excitability of layer 5 pyramidal neurons in the ILC but not PLC. Voltage traces recorded from layer 5 pyramidal neurons in PLC and ILC slices obtained from vehicle (black) scPCP-treated (red) mice by whole-cell patch clamp. The traces were recorded in response to −200 pA (hyperpolarizing) and +300 pA (depolarizing) current injections (resting potential: −70 mV). Right panels: Average of input-output curves. Note that scPCP treatment selectively increased excitability of ILC neurons.
Figure 3:
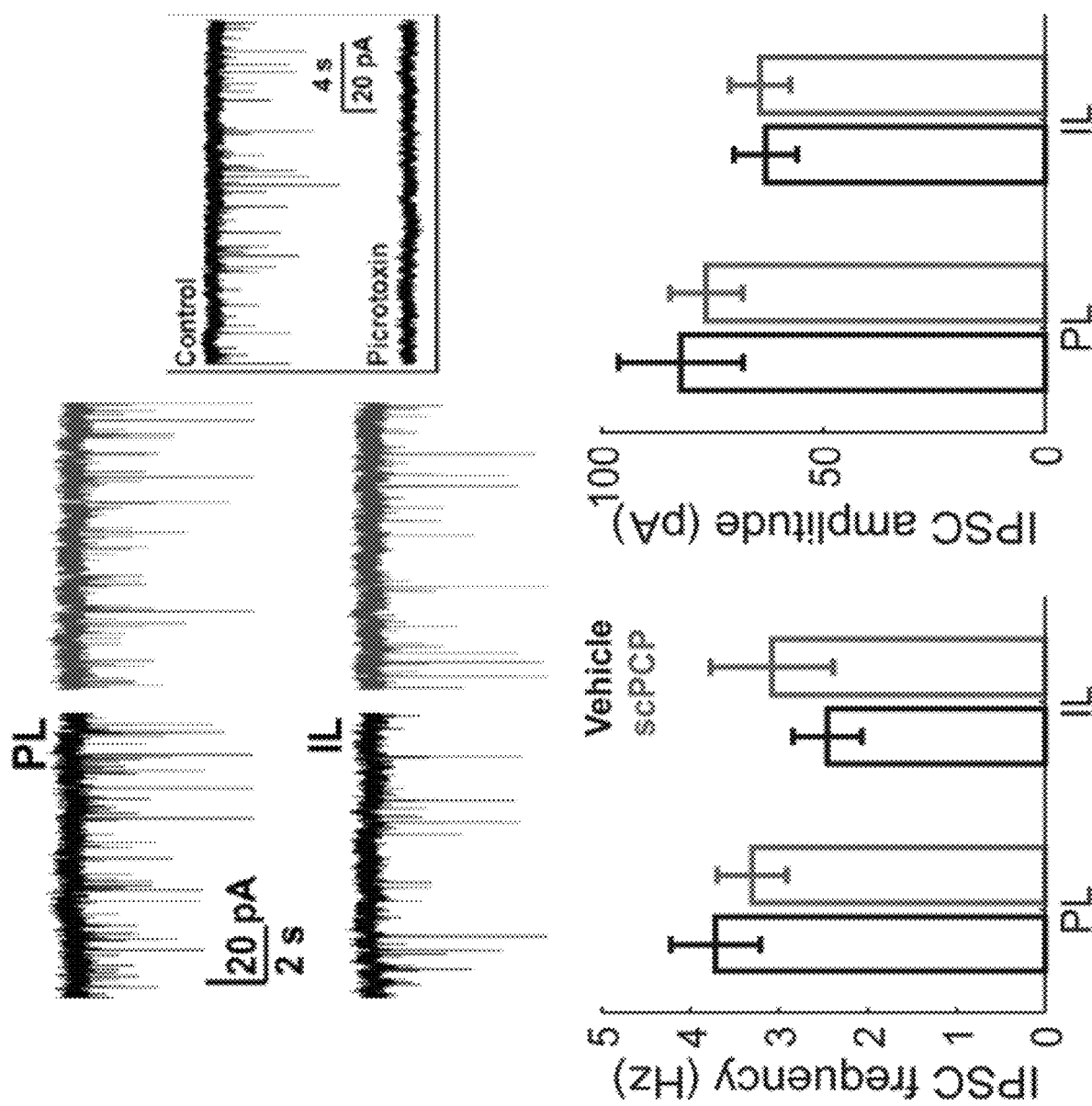
FIG. 3. GABAergic iPSPs measured using KCl internal solution are unaffected in the mPFC of scPCP mice. Whole-cell recordings of inhibitory synaptic currents at −85 mV from layer 5 pyramidal neurons in slices of the PLC and ILC obtained from vehicle (black traces) and PCP (red traces) treated mice by whole-cell patch clamp [inset: the currents were $GABA_A$ mediated and blocked by picrotoxin.] Right panels, Average IPSC frequency and amplitude.

To begin filling this gap, here we took advantage of the subchronic phencyclidine (scPCP) treatment, which is a well-established established rodent model of cognitive deficits in schizophrenia (Jentsch and Roth, 1999; Steeds et al. 2015) and performed patch clamp recordings from pyramidal neurons in acute slices of the IL cortex (ILC) and PL cortex (PLC). (FIG. 1). Analysis of the input/output function showed a small increase in the excitability of pyramidal neurons of the ILC, but not the PLC, in scPCP treated mice compared with vehicle treated animals (FIG. 2). scPCP treatment was observed to cause increased excitability of layer 5 pyramidal neurons in the ILC but not the PLC based on voltage traces recorded from layer 5 pyramidal neurons in PLC and ILC slices obtained from vehicle scPCP-treated mice by whole-cell patch clamp. (FIG. 2). scPCP treatment was observed to selectively increase excitability of ILC neurons.

Figure 4:
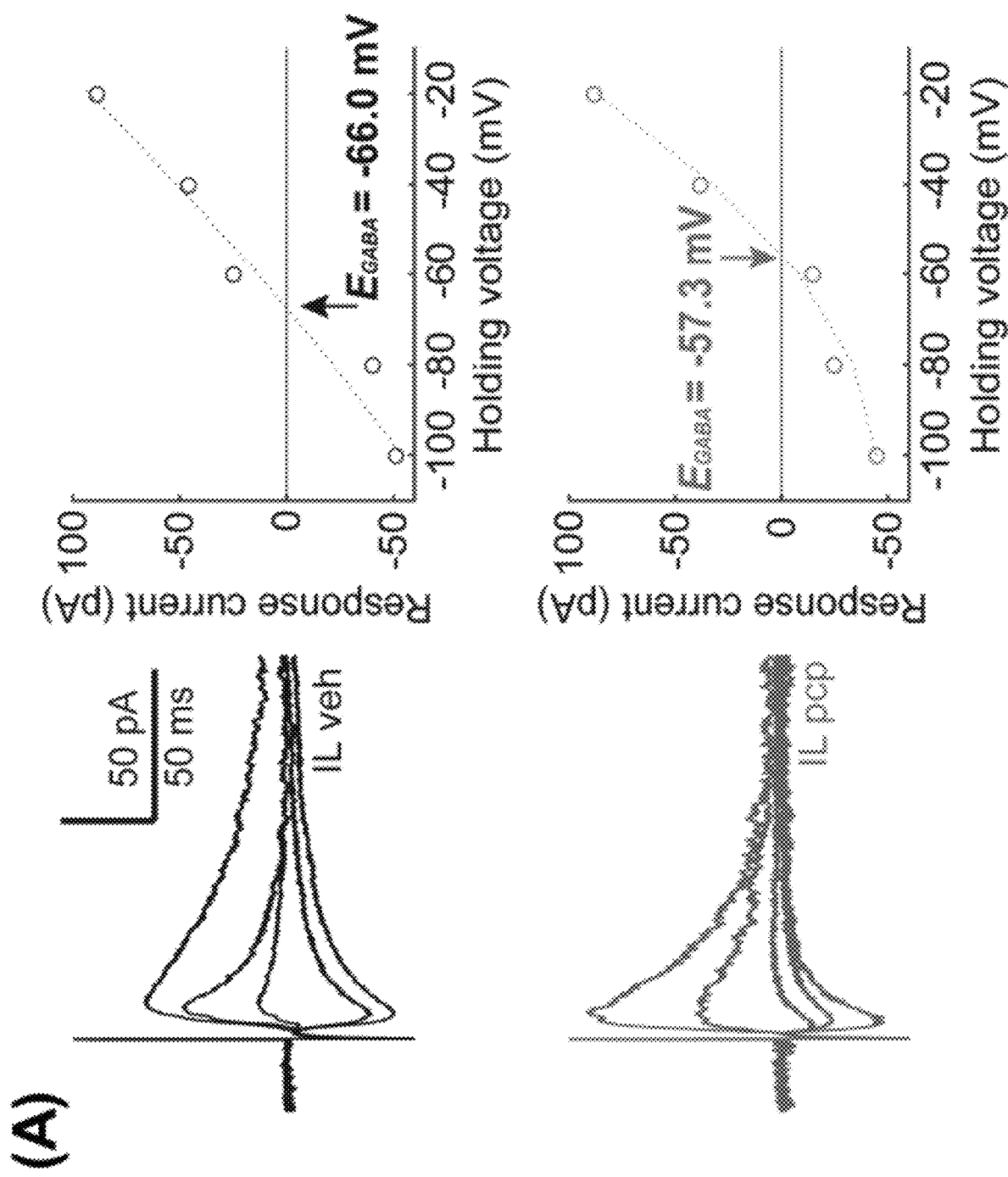
FIG. 4. (A) Left Panels: Example traces of $GABA_A$ current response by electrical stimulation in mPFC pyramidal neurons in control (top panel, black) and in scPCP (bottom, red). Bipolar electrode was put in layer 1, 100-200 um apart from recording site within layer2/3 with presence of 3 mM kynurenic acid to block any glutamatergic synaptic currents. The response was evoked by the same size of single stimulus (0.2-1 mA, 0.2 ms) at five different holding voltages (−100, −80, −60, −40, −20 mV) for each neuron. For each voltage, a neuron was tested multiple times and those 5-10 traces tested at the same voltage were averaged later for peak analysis. Stimulus artifacts are shown as trimmed vertical lines and five current traces tested at different voltages are aligned to 0 pA with their baseline. Right Panels: Example $GABA_A$ reversal potential ($E_{GABA}$) of a neuron in control (top panel, black) and in scPCP (bottom, red) calculated from traces shown in (A). For the individual neuron, the peak size of current responses was measured (maximal current peak if the evoked response is positive while minimal current peak if negative) and plotted by holding voltages. $E_{GABA}$ of the neuron is estimated by polynomial fitting (degree 2; dotted line) as the voltage where evoked $GABA_A$ current becomes 0 pA. Average of GABA equilibrium potential in mPFC of control versus scPCP mice. Dotted gray lines to present average resting potentials for each group, which were measured by whole-cell patch recordings from separated neuron groups (each n>7). From left to right, number of neurons: 13, 9, 8. * $p<0.05$, *** $<0.001$ by unpaired t-test. (B) Average $GABA_A$ reversal potentials in layer 2/3 and layer 5 of ILC of control and scPCP mice. For bumetanide-tested scPCP mice, intraperitoneal injection was performed to live animal (0.3 mg/kg) 30-40 minutes before dissecting brains. 10 uM bumetanide were perfused into mPFC slice in incubation chamber (over 1 hour) as well as recording chamber. Dotted gray lines represent the resting potentials, which were measured by whole-cell patch recordings in different sets of experiment (each n>7). Notice that bath application (in the holding and recording chambers) of the NKCC1 antagonist bumetanide normalizes the GABA reversal potential, which is again hyperpolarizing (Filled bars).
Figure 4:
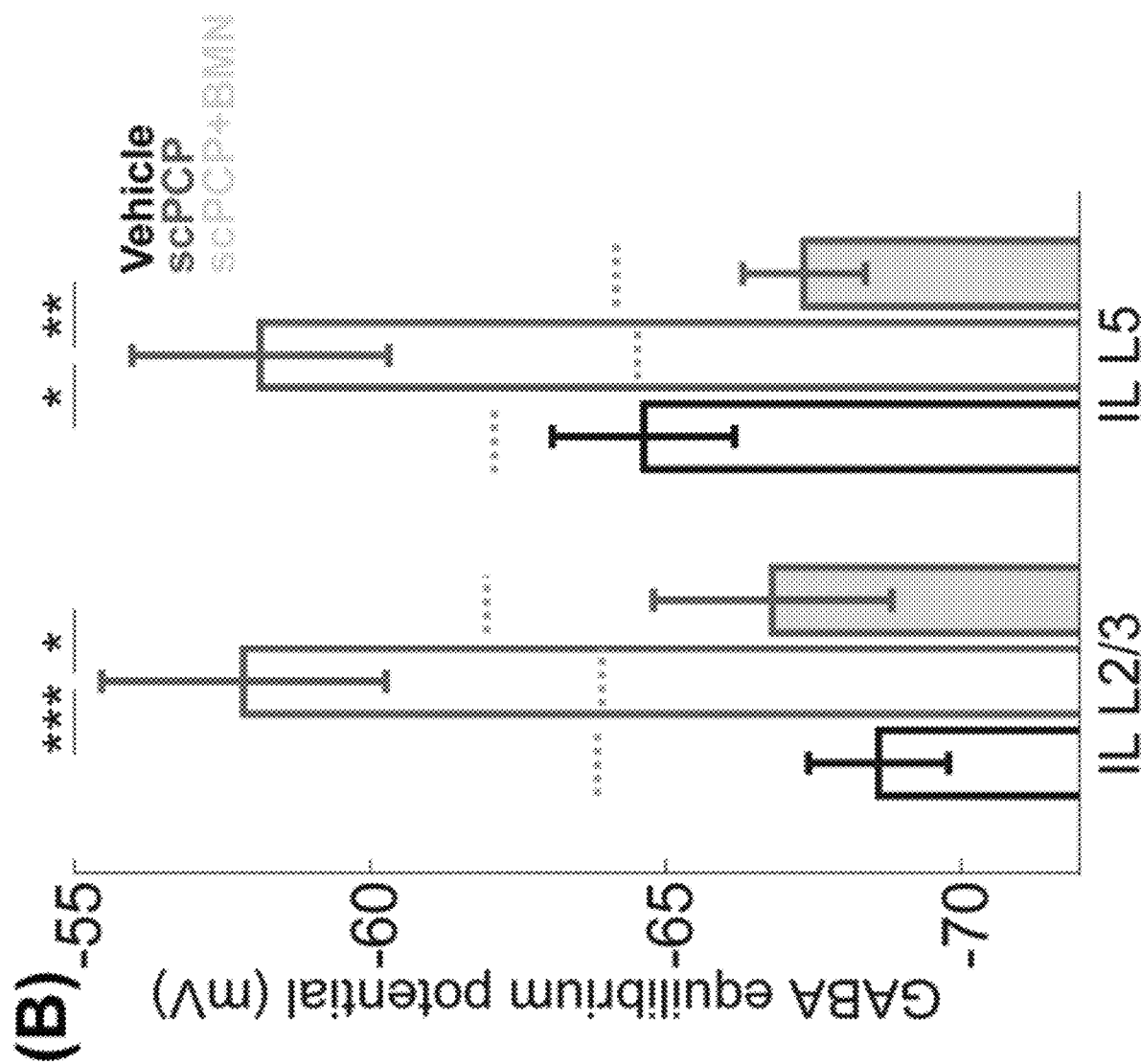
Figure 5:
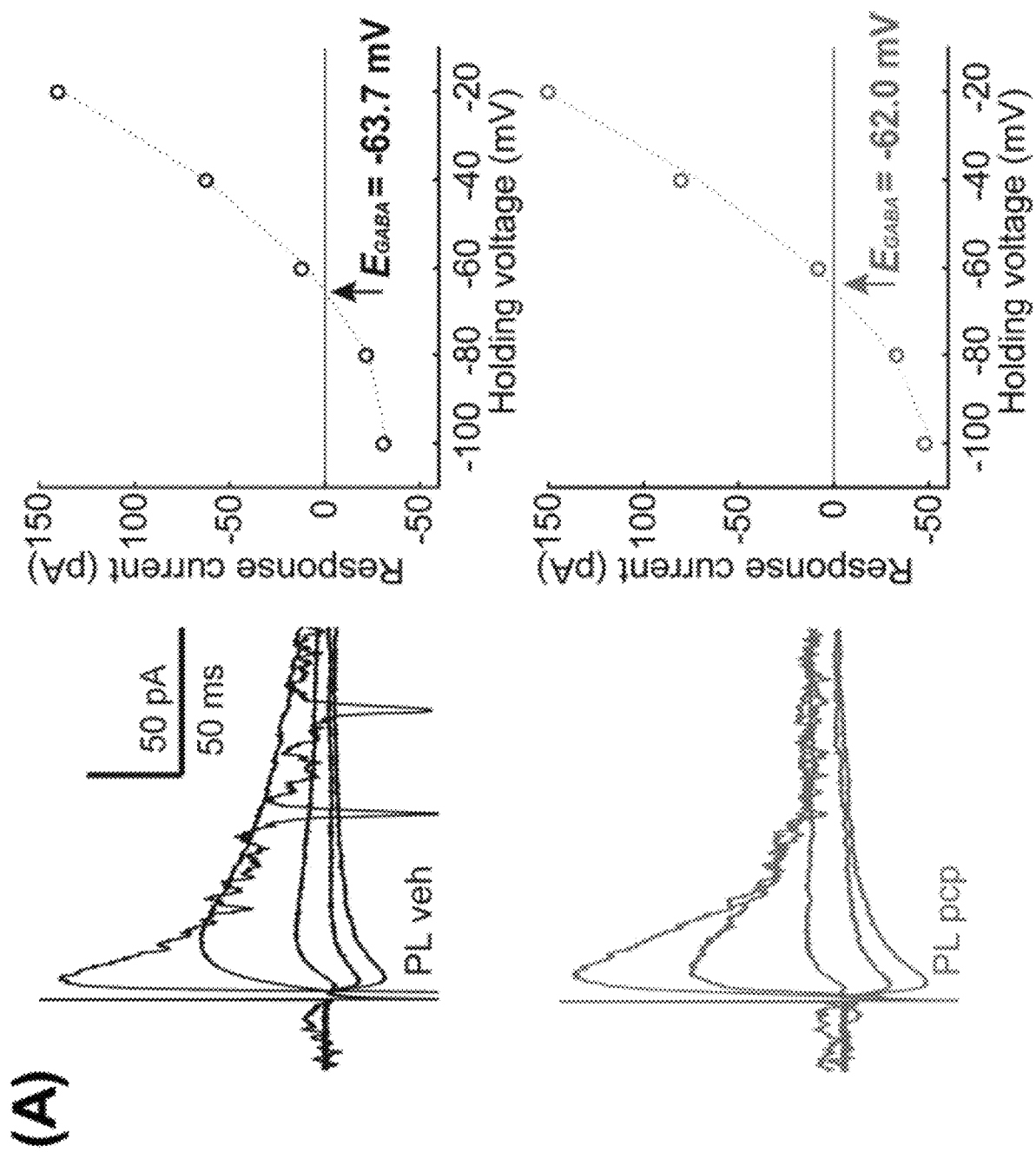
FIG. 5. The reversal potential of the $GABA_A$ current is unaffected in pyramidal neurons of the PLC of scPCP mice. A) Left panels: Perforated patch recordings of $GABA_A$ currents in layer 5 pyramidal neurons of the PLC from control mice (black traces) and scPCP mice (red traces). Right plots: reversal potentials and membrane resting potentials (dotted lines) of PLC pyramidal neurons. Same experimental conditions as in FIG. 4. B) GABA equilibrium potential mV.
Figure 5:
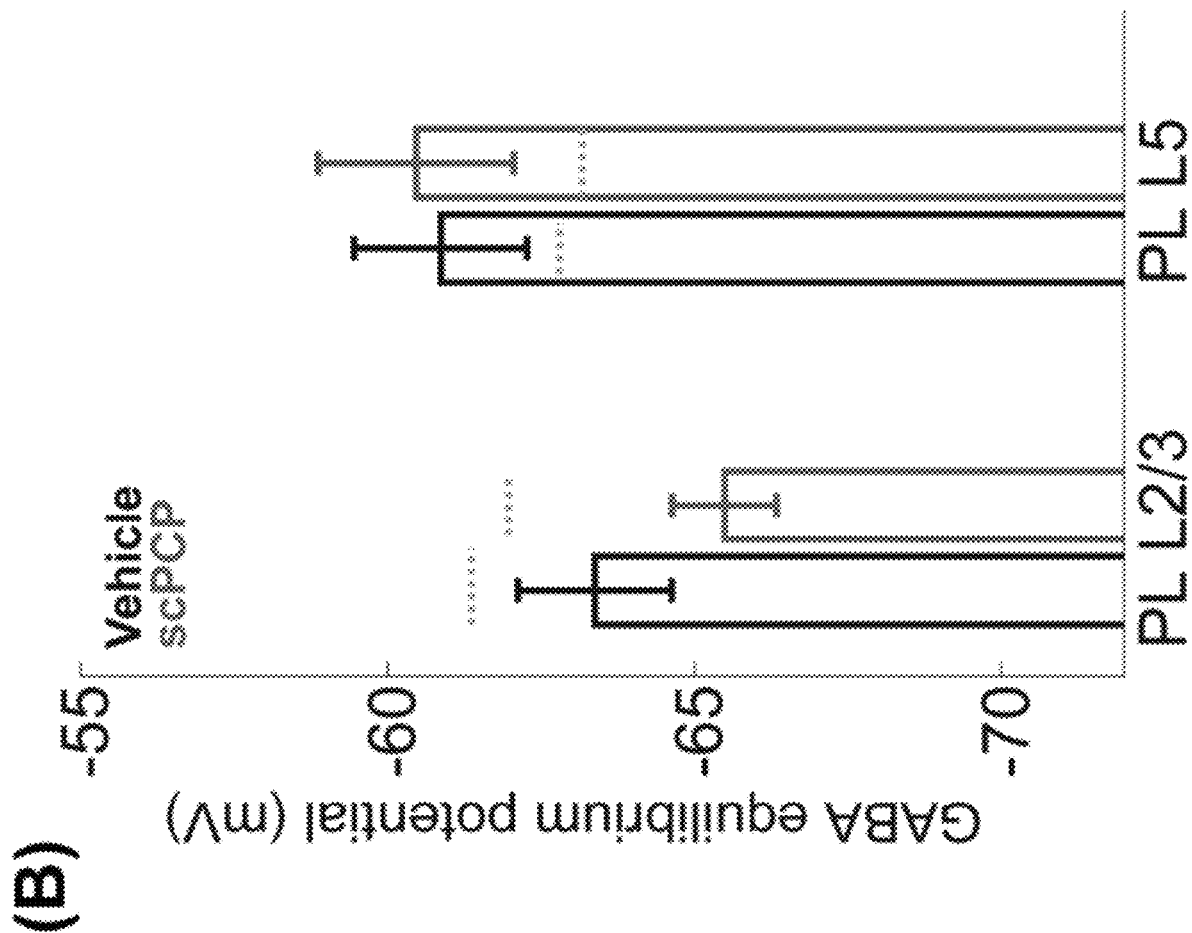

By performing whole-cell recordings of inhibitory synaptic currents at −85 mV from layer 5 pyramidal neurons in slices of the PLC and ILC obtained from vehicle and PCP treated mice by whole-cell patch clamp, we also observed that GABAergic iPSPs measured using KCl internal solution were unaffected in the mPFC of scPCP mice. As further illustrated in FIG. 4 and FIG. 5, the reversal potential of $GABA_A$-mediated currents is shifted toward depolarized potential in pyramidal neurons of the infralimbic prefrontal cortex.

Figure 6:
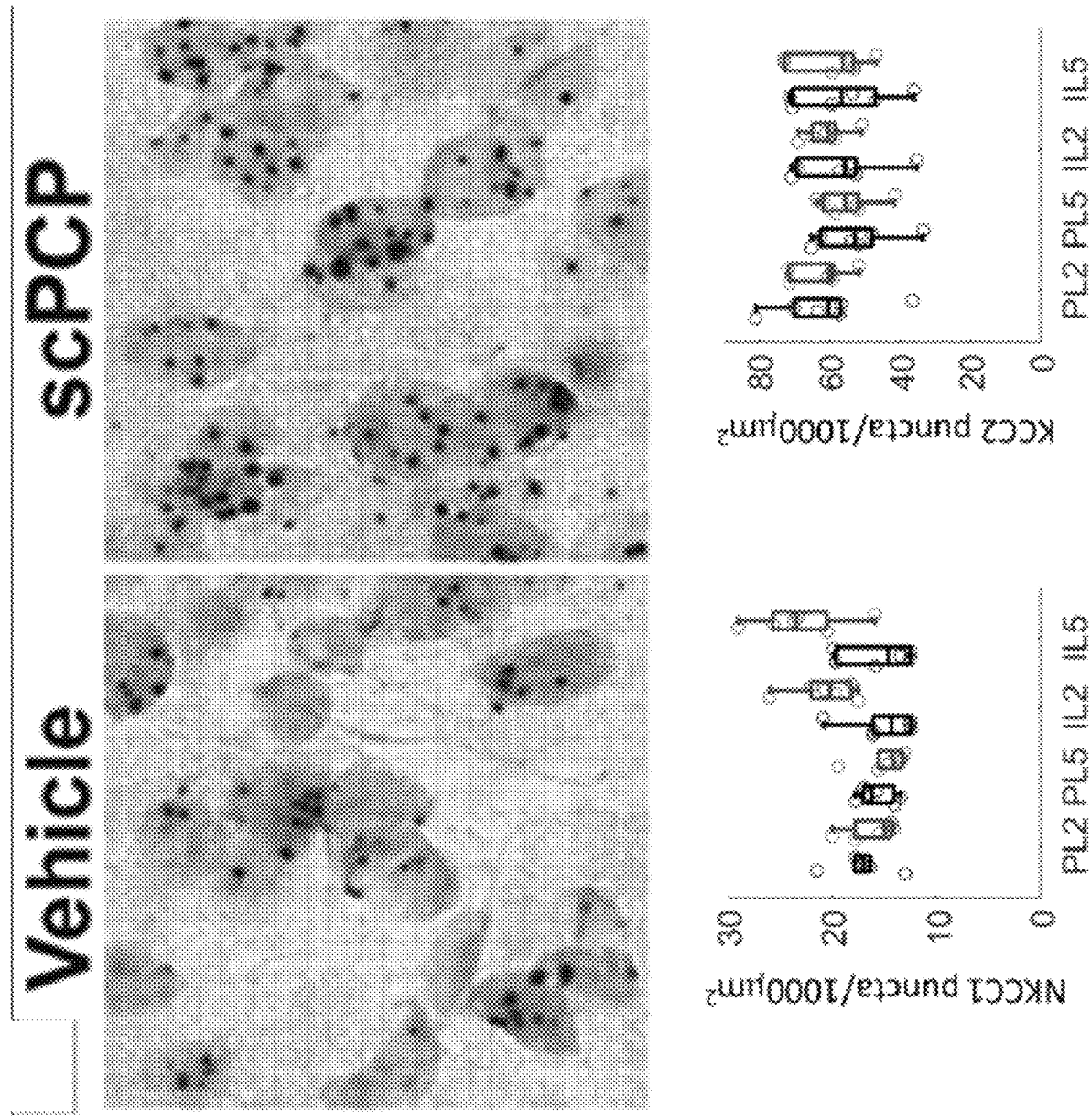
FIG. 6. Selective upregulation of the sodium-potassium-chloride cotransporter (NKCC1) in ILC of scPCP mice. (Top) In-situ hybridization image for NKCC1 (slc12a2) in layer 5 ILC pyramidal neurons of vehicle and scPCP mice (60×). Brown signals were detected NKCC1 mRNAs (slc12a2) by 3,3'-diaminobenzidine staining. Green area stained by methyl green shows cell bodies. (Bottom) Quantification of NKCC1 (slc12a2) and KCC2 (slc12a5) expression levels in control and scPCP mice. Each dot in the plot represents data obtained from one individual animal (average of counting in 3 cortical sections). Notice the large increase in NKCC1 expression in both layer 2.3 and layer 5 of the ILC (but not PLC). $p=0.0127$ for IL L2 (6 vehicle vs 6 pcp); $p=0.00959$ for IL L5 (6 vehicle vs 6 pcp). No differences were found for KCC2 expression.

We then performed in situ hybridization to quantify gene expression in the PFC tissue and found that expression of the transcript encoding for the NKCC1 transporter is increased in PCP-treated animals. (FIG. 6). This shift in the reversal potential of the $GABA_A$ current has dramatic functional consequences, as it causes the $GABA_A$ current, which in physiological conditions is the main inhibitory current in the adult brain, to become excitatory. We found that in pyramidal neurons of the infralimbic (IL), but not the prelimbic (PL) subdivision of the medial prefrontal cortex show excitatory $GABA_A$ currents. We further found that pharmacological inhibition of NKCC1 with bumetanide normalizes the $GABA_A$-mediated current reversal potential ex-vivo and, most importantly, rescues cognitive function in-vivo.

Figure 7:
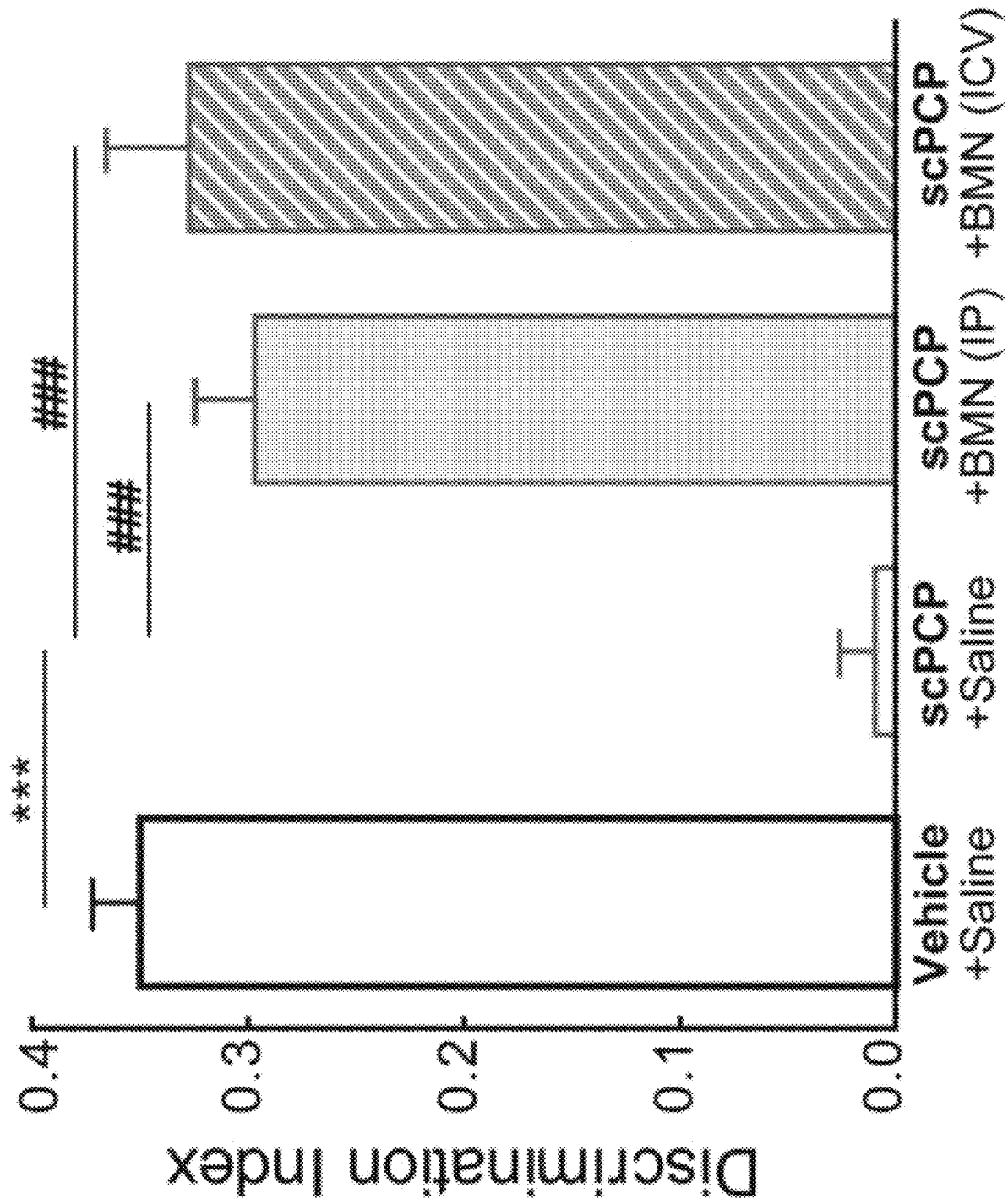
FIG. 7. Bumetanide treatment rescues the cognitive impairment in scPCP mice. Discrimination index calculated from novel object recognition tests. Notice that bumetanide (both 0.3 mg/ml; icy, and 0.1 mg/kg; ip) completely rescues scPCP-induced NOR deficit in male C57BL/6J mice. 10 mice were measured for each experimental group.
Figure 8:
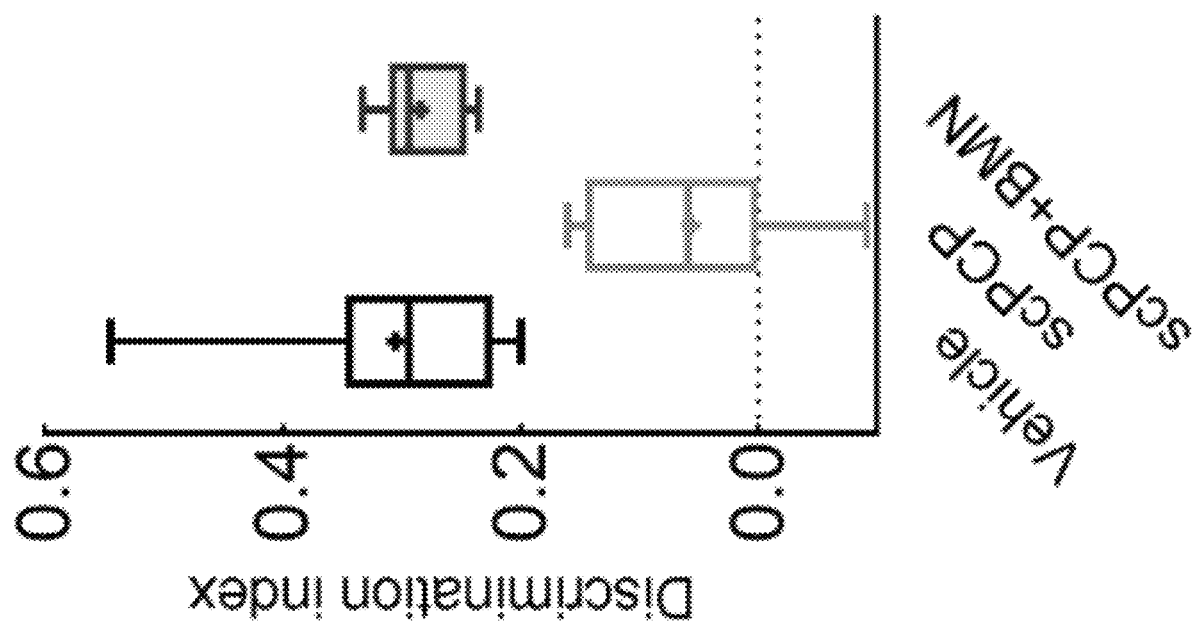
FIG. 8. Bumetanide rescues Novel Object Recognition task in female scPCP mice. A single dose of bumetanide (IP) given to female C57BL/6J mice, significantly rescued sc-PCT-induced deficits in the Novel Object Recognition test. Data are from 9 mice per group. One-way ANOVA followed by post-hoc bonferroni correction was done where significance was observed. $p<0.01$. (Additional data not shown).

Oral administration of a single dose of bumetanide completely rescues the performance of PCP-treated mice in the novel object recognition task, a classical test used to evaluate memory. (FIG. 7). Bumetanide given as a single dose (IP) also rescued novel object recognition in female scPCP mice. (FIG. 8). This finding has immediate translational value, as bumetanide is an already approved drug. Additionally, we also measured the $GABA_A$ reversal potential in IL pyramidal cells from PCP animals treated with the atypical antipsychotic lurasidone, which also rescues the behavior. Interestingly $GABA_A$ reversal was still shifted in these mice, suggesting that the bumetanide and lurasidone act through different mechanisms and thus may have synergistic effects.

In keeping with these observations, in vivo, Bumetanide (0.3 mg/ml; icy) significantly blocked PCP- (10 mg/kg) as well as amphetamine- (2.5 mg/kg) induced increase in locomotor activity in scPCP-treated mice. This can be interpreted as evidence for ability to treat delusions and hallucinations in psychotic disorders, including schizophrenia, major depression, bipolar disorder, various dementias, including vascular dementia and other neurodegenerative disorders. These finding have immediate translational value, as bumetanide is an already approved drug that could be promptly used to improve cognition in patients with cognitive impairment, psychosis, or negative symptoms in the disorders cited above.

Bumetanide prevented the development of cognitive impairment when give prior to one weeks treatment with PCP. This is evidence that bumetanide could prevent the onset of cognitive impairment in schizophrenia and bipolar disorder. Subeffective doses of bumetanide in the PCP model of cognitive impairment became effective when combined with a subeffective dose of a dopamine D1 agonist (e.g., SKF38393) or a subeffective dose of a $GABA_A$ agonist (e.g., gaboxadol). Subeffective doses of bumetanide in the NOR deficit $CaMKII\alpha^{+/-}$ mice model became effective when combined with a subeffective dose of a dopamine D1/D2 antagonist (e.g., risperidone). The discovery of these synergistic actions which will have value in the treatment of many neuropsychiatric disorders. Neurosteroids such as allopregnanolone is a GABA A agonist which could be used clinically with bumetanide to treat post-partum depression, other forms of depression.

Bumetanide was effective in restoring social interaction in the PCP treated mouse which is an indication it will be effective to treat negative symptoms in patients with schizophrenia.

Figure 9:
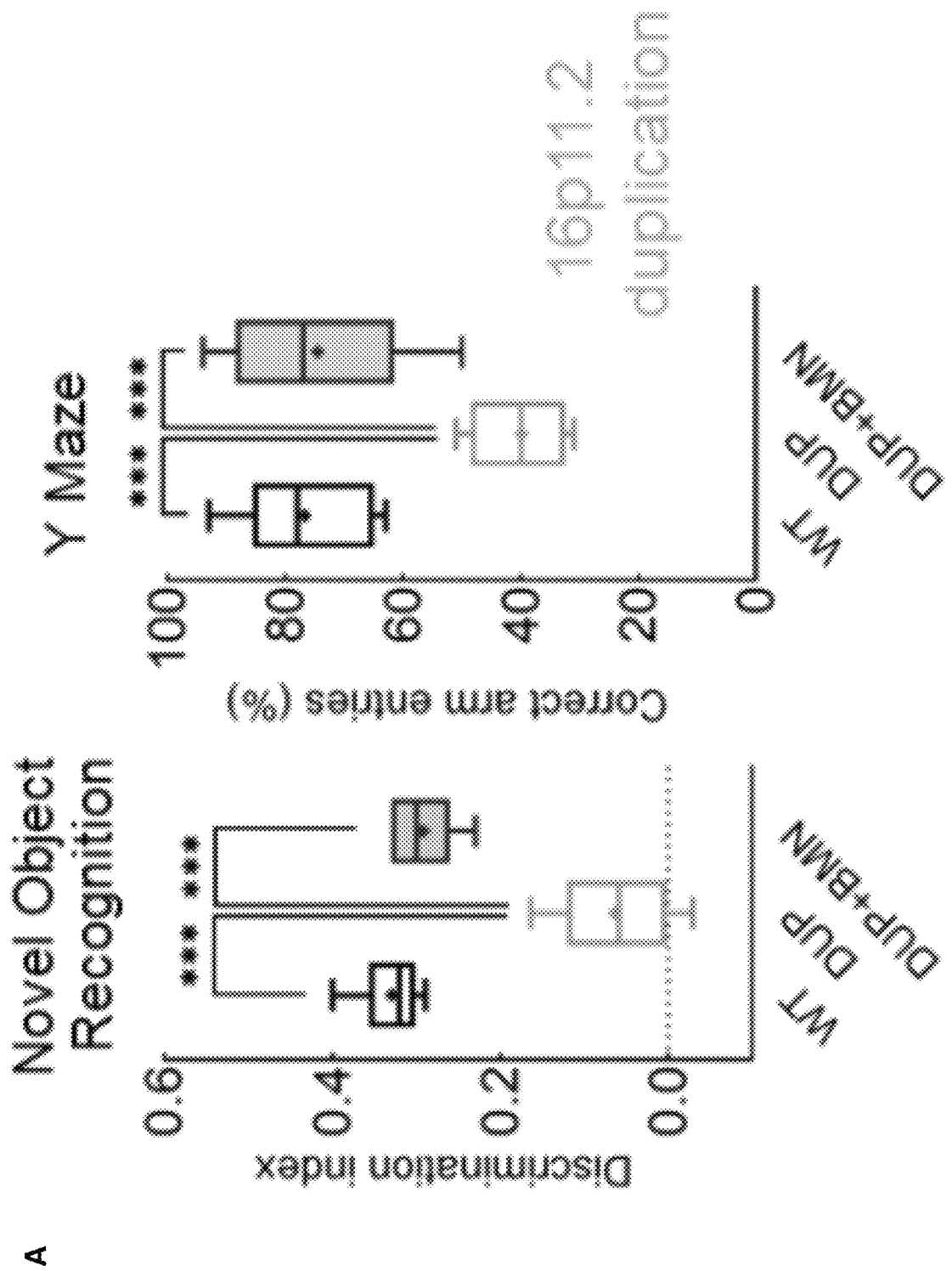
FIG. 9. Bumetanide ameliorates cognitive performance in (A) 16p11.2DUP mice and (B) CaMK2A$^{+/-}$ mice. In both mouse models NOR and Y maze performance were significantly impaired compared to WT littermates, and completely rescued by bumetanide (0.1 mg/kg, ip); n=4 in each group. ***$p<0.001$. (Additional data not shown).
Figure 9:
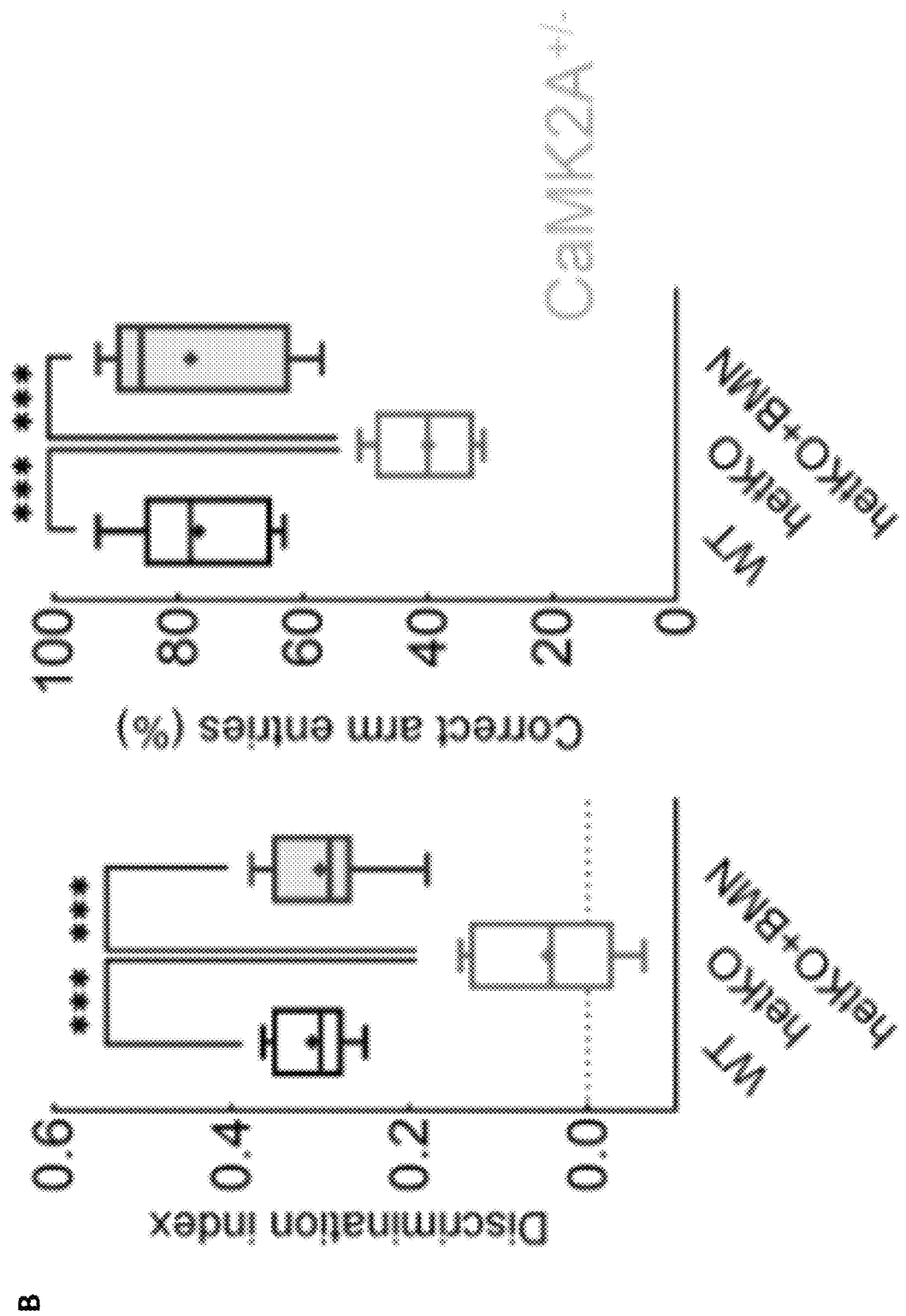
Figure 10:
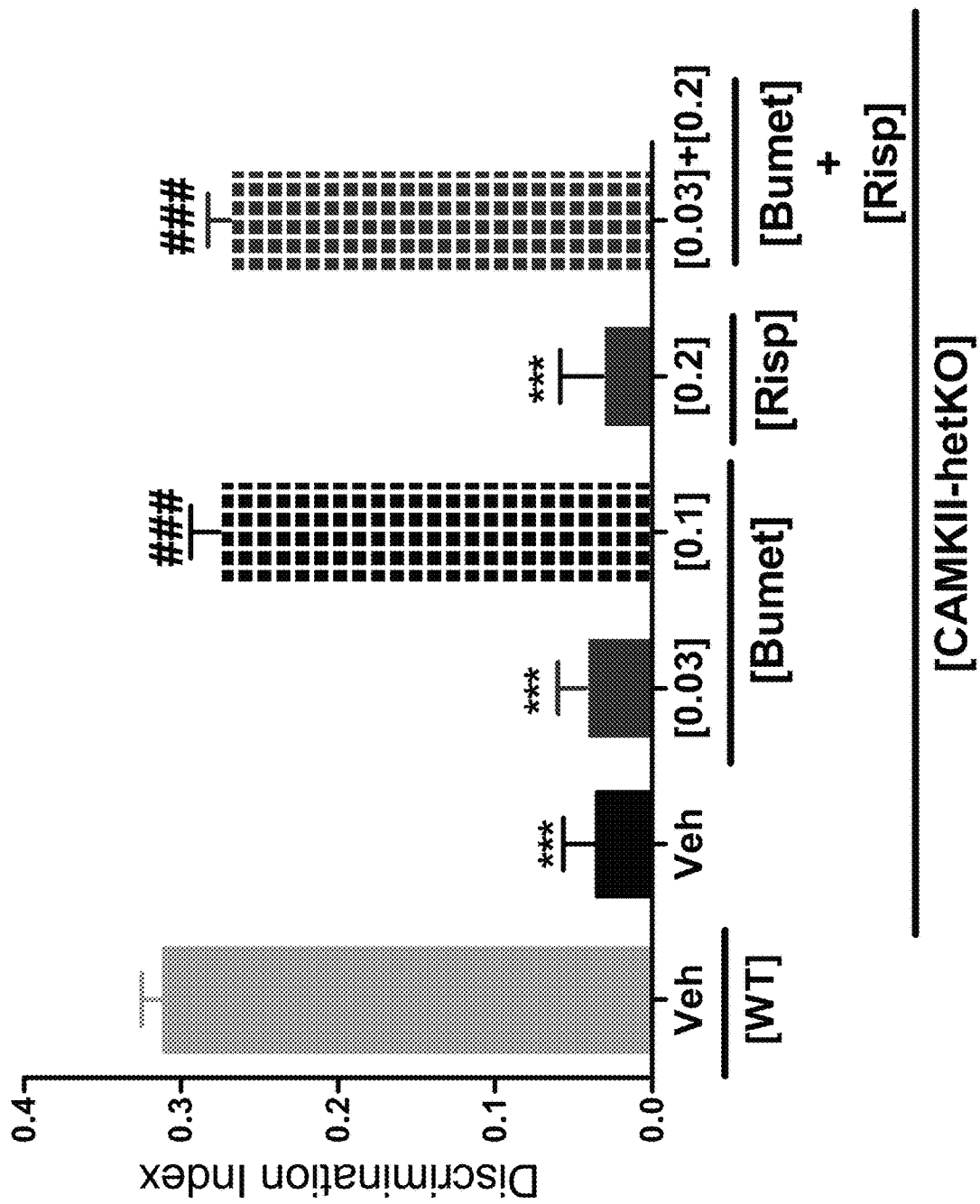
FIG. 10. The combination of sub-effective dose bumetanide and ineffective dose risperidone significantly potentiates the rescue of NOR deficit in CaMKIIα$^{+/-}$ mice. Data are shown as mean±S.E.M. n=8/group, one-way ANOVA followed by post-hoc Bonferroni correction where significance was observed. ***$p<0.001$—significant decrease in discrimination index vs. WT+veh, indicating lack of efficacy. ###$p<0.001$: significant increase in discrimination index vs. CaMKIIα$^{+/-}$ +veh, indicating significant efficacy to rescue NOR deficit.

Bumetanide also was observed to improve cognitive performance in two genetic models of cognitive impairment, including the CaMK2A+/−mouse model and the 16p11.2 duplication mouse model. (See Yamasaki et al., "Alpha-CaMKII deficiency causes immature dentate gyrus, a novel candidate endophenotype of psychiatric disorders," Molecular Brain, 1 (2008) 6; and McCarthy et al., "Microduplications of 16p11.2 are associated with schizophrenia," Nat. Gene., 41 (2009) 1223-1227; respectively). Both models are relevant to human conditions. CaMK2A loss causes cognitive dysfunction and has been implication in psychiatric disorders including schizophrenia. (See Yamasaki et al., "Alpha-CaMKII deficiency causes immature dentate gyrus, a novel candidate endophenotype of psychiatric disorders," Molecular Brain, 1 (2008) 6; Kool et al., "CAMK2-dependent Signaling in Neurons is Essential for Survival," J. Neuroscience: the official journal of the Society for Neuroscience, 39 (2019) 5424-5439; and Papaleo et al., "Mouse models of genetic effects on cognition: relevance to schizophrenia," Neuropharmacology, 62 (2012) 1204-1220). In addition, studies in two large human cohorts found that microduplication of a 600-kb regions of chromosome 16p11.2 results in increased risk of psychiatric diagnosis and ADHD. (See Niarchou et al., "Psychiatric disorders in children with 16p11.2 deletion and duplication," Translational psychiatry, 9 (2019) 8). Our data show that subjects in the two different genetic mouse models of cognitive impairment equally benefit from treatment with bumetanide. (FIG. 9). We also observed that the combination of a sub-effective dose of bumetanide and an ineffective dose of risperidone significantly potentiates the rescue of NOR deficit in $CaMKII\alpha^{+/-}$ mice. (FIG. 10).

Summary $GABA_A$ current reversal potential in IL neurons shifts from being hyperpolarization to depolarizing with low-dose PCP treatment. This change is limited to the ILC, while no effect is detected in the PLC. This is both an important internal control for the recordings and an intriguing hint of the underlying network changes. The depolarizing shift is mediated by selective increase in NKCC1 expression, while KCC2 expression is unaffected (also an important internal control). The NKCC1 antagonist bumetanide normalizes $GABA_A$ reversal in acute ILC slices. In vivo, bumetanide completely reverses the cognitive impairments in scPCP mice. Considering that bumetanide is already an FDA approved drug, this finding may rapidly be translated to the clinical setting.

Methods

Routine for mPFC recording. 3 week-old mice were injected with saline (vehicle) or PCP (0.1 mg/kg) two times a day for 7 consecutive days and rested for another 7 days without injections. They were then sacrificed for recordings within 7 days.

30 to 40 day-old mice were anesthetized with isoflurane and sacrificed by decapitation. The brain was removed from the skull in ice-cold artificial cerebrospinal fluid (ACSF) equilibrated with 95% O2 and 5% CO2 (pH 7.4). Coronal, 300 μm thick, slices of the medial prefrontal cortex were cut using a vibroslicer and stored in ACSF solution. The bath temperature was kept at 31-32° C. The solution flow was kept at −3 ml/min.

Gramicidine internal solution. 50 ug of gramicidin was added to 1 ml of potassium gluconate internal solution which as warmed up to 35° C. in advance. The solution ultrasonicated for 15 minutes and filtered. Prepared gramicidin solution was used within 2 hours. The tip of recording pipettes (3-6 MOhm) were filled with the plain K-gluconate internal solution first and then backfilled with gramicidin internal solution. When approaching cell, smaller positive pressure is applied than whole-cell patch clamp and giga seal was formed as quickly as possible.

Lucifer yellow for perforated patch visualizing. We used 0.1% lucifer yellow in internal solution to visually confirm in real time if the membrane is not ruptured so that stablized in perforated patch condition. In this condition, the access resistance is usually in 80-150 MOhm range.

RNAscope in situ hybridization assay. Anesthetized vehicle and scPCP mice (same aged used in perforated patch recording) were perfused with 4% paraformadehyde and post-fixation overnight in the same solution and then moved into 30% sucrose with 0.1% diethyl pyrocarbonate. Coronal sections (14 um) containing mPFC were cut on dry ice using microtome and mounted on positively charged glass slides. After pre-treatment by hydrogen peroxide and proteinase K, NKCC1 and KCC2 probes were hybridized for 2 hours at 40° C. and signals were amplified using single probe assay kit reagents. The signal (brown dots developed by 3,3'-diaminobenzidine staining) was counted using StereoInvestigator on 63× oil immersion objective image. Frame size: 40×40 um2 counting frame in 100×100 um2 grid for NKCC1, 20×20 in 80×80 for KCC2. Three mPFC sections, apart 350 um from each on anterior-posterior axis were used for counting from a single animal and the average of three was reported as the expression level.

REFERENCES

Aas et al. (2014) "A systematic review of cognitive function in first-episode psychosis, including a discussion on childhood trauma, stress, and inflammation." Front Psychiatry. 2014 Jan. 8; 4:182. doi: 10.3389/fpsyt.2013.00182. Review.

Barbas and Garcia-Cabezas (2016) "How the prefrontal executive got its stripes." Curr Opin Neurobiol. 2016 October; 40:125-134. doi: 10.1016/j.conb.2016.07.003. Epub 2016 Jul. 29.

Ben-Ari et al. (1989) "Giant synaptic potentials in immature rat CA3 hippocampal neurones." J Physiol. 1989; 416: 303-325.

Benes (1999) "Evidence for altered trisynaptic circuitry in schizophrenic hippocampus," Biol Psychiatry. 1999 Sep. 1; 46(5):589-99. Review.

Cherubini et al. (1991) "GABA: an excitatory transmitter in early postnatal life." Trends Neurosci. 1991 December; 14(12):515-9. Review.

Cohen et al. (2002) "On the origin of interictal activity in human temporal lobe epilepsy in vitro." Science. 2002 Nov. 15; 298(5597):1418-21.

Deidda et al. (2015). "Reversing excitatory GABAAR signaling restores synaptic plasticity and memory in a mouse model of Down syndrome." Nat. Med. 21, 318-326 (2015).

Green and Harvey. "Cognition in schizophrenia: Past, present, and future." Schizophr Res Cogn. Author manuscript; available in PMC 2014 Sep. 22.

Kaneko and Keshavan (2012) "Cognitive Remediation in Schizophrenia. Clin Psychopharmacol Neurosci." 2012 December; 10(3): 125-135.

Kohli et al. (2019) "Oxytocin attenuates phencyclidine hyperactivity and increases social interaction and nucleus accumben dopamine release in rats." Neuropsychopharmacology. 2019 January; 44(2):295-305. doi: 10.1038/s41386-018-0171-0. Epub 2018 Aug. 7.

Kool et al., "CAMK2-dependent Signaling in Neurons is Essential for Survival," J. Neuroscience: the official journal of the Society for Neuroscience, 39 (2019) 5424-5439.

Lepage et al. (2014) "In review neurocognition: clinical and functional outcomes in schizophrenia." Can. J. Psychiatry. 2014; 59(1):5-12.

Lewis et al. (1999) "Altered GABA neurotransmission and prefrontal cortical dysfunction in schizophrenia. Biol Psychiatry. 1999 Sep. 1; 46(5):616-26. Review.

Lewis et al. (2005) "Cortical inhibitory neurons and schizophrenia." Nat Rev Neurosci. 2005 April; 6(4):312-24. Review.

McCarthy et al., "Microduplications of 16p11.2 are associated with schizophrenia," Nat. Gene., 41 (2009) 1223-1227

McLean et al. (2017) "Dopamine dysregulation in the prefrontal cortex relates to cognitive deficits in the subchronic PCP-model for schizophrenia: A preliminary investigation." J Psychopharmacol. 2017 June; 31(6): 660-666. doi: 10.1177 /0269881117704988. Epub 2017 Apr. 26.

Niarchou et al., "Psychiatric disorders in children with 16p11.2 deletion and duplication," Translational psychiatry, 9 (2019) 8.

Papaleo et al., "Mouse models of genetic effects on cognition: relevance to schizophrenia," Neuropharmacology, 62 (2012) 1204-1220).

Rannals et al. (2016) "Neurodevelopmental models of transcription factor 4 deficiency converge on a common ion channel as a potential therapeutic target for Pitt Hopkins syndrome." Rare Dis. 2016 Aug. 5; 4(1):e1220468. doi: 10.1080/21675511.2016.1220468. eCollection 2016.

Vertes (2006). "Interactions among the medial prefrontal cortex, hippocampus and midline thalamus in emotional and cognitive processing in the rat." Neuroscience. 2006 Sep. 29; 142(1):1-20. Epub 2006 Aug. 2. Review.

Vöhringer et al. (2013) "Cognitive impairment in bipolar disorder and schizophrenia: a systematic review." Frontiers in Psychiatry, 4, 87.

Yamasaki et al., "Alpha-CaMKII deficiency causes immature dentate gyrus, a novel candidate endophenotype of psychiatric disorders," Molecular Brain, 1 (2008) 6.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/ or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating cognitive deficits in a subject having schizophrenia, bipolar disorder, or psychiatric depression, and exhibiting cognitive deficits, the method comprising administering to the subject (i) an effective amount of an antagonist of the $Na^+$-$K^+$-$2Cl^-$ cation-chloride cotransporter isoform 1 (NKCC1) and (ii) a subeffective amount of an agonist of the dopamine D1 receptor, a subeffective amount of an agonist of the $GABA_A$ receptor, or a subeffective amount of an antagonist of the dopamine D1/D2 receptor for treating the cognitive deficits in the subject having schizophrenia, bipolar disorder, or psychiatric depression and exhibiting cognitive deficits.

2. The method of claim 1, wherein the antagonist of NKCC1 is selected from the group consisting of bumetanide, furosemide, piretanide, benzmetanide, azosemide, torasemide (torsemide), tripamide, and tizolemide.

3. The method of claim 1 comprising administering to the subject the subeffective amount of the agonist of the dopamine D1 receptor.

4. The method of claim 3, wherein the agonist of the dopamine D1 receptor is selected from A-86929, dihydrexidine, dinapsoline, dinoxyline, doxanthrine, SKF-81297, SKF-82958, SKF-38393, fenoldopam, 6-Br-APB, stepholidine, A-68930, A-77636, CY-208,243, SKF-89145, SKF-89626, 7,8-dihydroxy-5-phenyl-octahydrobenzo[h]isoquinoline, cabergoline, and pergolide.

5. The method of claim 3, wherein the agonist of the dopamine D1 receptor is SKF-38393.

6. The method of claim 1, comprising administering to the subject the subeffective amount of the agonist of the $GABA_A$ receptor.

7. The method of claim 6, wherein the agonist of the $GABA_A$ receptor is selected from the group consisting of ADX-71441, alcohols, avermectins, babamide, baclofen, barbiturates, bamaluzole, benzodiazepines, bromides, 1,4-butanediol, carbamates, chloralose, chlormezanone, clomethiazole, dihydroergolines, etazepine, etifoxine, GABA, gabamide, GABOB, gaboxadol, gamma-butyrolactone (GBL), gamma-hydroxybutyric acid (GHB), gamma-hydroxyvaleric acid (GHV), gamma-valerolactone (GVL), ibotenic acid, imidazoles, isoguvacine, isonipecotic acid, kavalactones, lesogaberan, loreclezole, muscimol, neuroactive steroids, non-benzodiazepines, petrichloral, phenibut, picamilon, piperidinediones, progabide, propanidid, propofol, pyrazolopyridines, quinazolinones, quisqualamine, SL-75102, stiripentol, sulfonylalkanes, thiomuscimol, tolgabide, valerian constituents, volatiles/gases, and zolpidem.

8. The method of claim 6, wherein the agonist of the $GABA_A$ receptor is gaboxadol.

9. The method of claim 6, wherein the agonist of the $GABA_A$ receptor is allopregnanolone.

10. A method for treating cognitive deficits in a subject having schizophrenia and exhibiting cognitive deficits, the method comprising administering to the subject an effective amount of an antagonist of the $Na^+$-$K^+$-$2Cl^-$ cation-chloride cotransporter isoform 1 (NKCC1) and (ii) a subeffective amount of an agonist of the dopamine D1 receptor, a subeffective amount of an agonist of the $GABA_A$ receptor, or a subeffective amount of an antagonist of the dopamine D1/D2 receptor for treating the cognitive deficits in the subject having schizophrenia and exhibiting cognitive deficits.

11. The method of claim 10, wherein the antagonist of NKCC1 is selected from the group consisting of bumetanide, furosemide, piretanide, benzmetanide, azosemide, torasemide (torsemide), tripamide, and tizolemide.

12. The method of claim 10 comprising administering to the subject the subeffective amount of the agonist of the dopamine D1 receptor.

13. The method of claim 12, wherein the agonist of the dopamine D1 receptor is SKF-38393.

14. The method of claim 10, comprising administering to the subject the subeffective amount of the agonist of the $GABA_A$ receptor.

15. The method of claim 14, wherein the agonist of the $GABA_A$ receptor is selected from the group consisting of ADX-71441, alcohols, avermectins, babamide, baclofen, barbiturates, bamaluzole, benzodiazepines, bromides, 1,4-butanediol, carbamates, chloralose, chlormezanone, clomethiazole, dihydroergolines, etazepine, etifoxine, GABA, gabamide, GABOB, gaboxadol, gamma-butyrolactone (GBL), gamma-hydroxybutyric acid (GHB), gamma-hydroxyvaleric acid (GHV), gamma-valerolactone (GVL), ibotenic acid, imidazoles, isoguvacine, isonipecotic acid, kavalactones, lesogaberan, loreclezole, muscimol, neuroactive steroids, non-benzodiazepines, petrichloral, phenibut, picamilon, piperidinediones, progabide, propanidid, propofol, pyrazolopyridines, quinazolinones, quisqualamine, SL-75102, stiripentol, sulfonylalkanes, thiomuscimol, tolgabide, valerian constituents, volatiles/gases, and zolpidem.

16. The method of claim 13, wherein the agonist of the $GABA_A$ receptor is gaboxadol.

17. The method of claim 13, wherein the agonist of the $GABA_A$ receptor is allopregnanolone.

18. A method for treating cognitive deficits in a subject having schizophrenia and exhibiting cognitive deficits, the method comprising administering to the subject (i) an effective amount of bumetamide and (ii) a subeffective amount of an agonist of the dopamine D1 receptor, a subeffective amount of an agonist of the $GABA_A$ receptor, or a subeffective amount of an antagonist of the dopamine D1/D2 receptor for treating the cognitive deficits in the subject having schizophrenia and exhibiting cognitive deficits.

19. The method of claim 18, further comprising administering to the subject an agonist of the dopamine D1 receptor.

20. The method of claim 19, wherein the agonist of the dopamine D1 receptor is SKF-38393.

21. The method of claim 18, further comprising administering to the subject an agonist of the $GABA_A$ receptor.

22. The method of claim 21, wherein the agonist of the $GABA_A$ receptor is selected from the group consisting of ADX-71441, alcohols, avermectins, babamide, baclofen, barbiturates, bamaluzole, benzodiazepines, bromides, 1,4-butanediol, carbamates, chloralose, chlormezanone, clomethiazole, dihydroergolines, etazepine, etifoxine, GABA, gabamide, GABOB, gaboxadol, gamma-butyrolactone (GBL), gamma-hydroxybutyric acid (GHB), gamma-hydroxyvaleric acid (GHV), gamma-valerolactone (GVL), ibotenic acid, imidazoles, isoguvacine, isonipecotic acid, kavalactones, lesogaberan, loreclezole, muscimol, neuroactive steroids, non-benzodiazepines, petrichloral, phenibut, picamilon, piperidinediones, progabide, propanidid, propofol, pyrazolopyridines, quinazolinones, quisqualamine, SL-75102, stiripentol, sulfonylalkanes, thiomuscimol, tolgabide, valerian constituents, volatiles/gases, and zolpidem.

23. The method of claim 21, wherein the agonist of the $GABA_A$ receptor is gaboxadol.

24. The method of claim 21, wherein the agonist of the $GABA_A$ receptor is allopregnanolone.

25. The method of claim 1, wherein the effective amount of the antagonist of NKCC1 is a subeffective amount of the antagonist of NKCC1 when administered without the subeffective amount of an agonist of the dopamine D1 receptor, the subeffective amount of an agonist of the $GABA_A$ receptor, or the subeffective amount of an antagonist of the dopamine D1/D2 receptor.

26. The method of claim 25, wherein the antagonist of NKCC1 is bumetanide.

* * * * *

UNITED STATES PATENT AND TRADEMARK OFFICE
CERTIFICATE OF CORRECTION

PATENT NO. : 11,666,547 B2
APPLICATION NO. : 16/915746
DATED : June 6, 2023
INVENTOR(S) : Marco Martina et al.

Page 1 of 1

It is certified that error appears in the above-identified patent and that said Letters Patent is hereby corrected as shown below:

In the Specification

Column 3, Line 62, "icy" should be --icv--.

Column 15, Line 9, "icy" should be --icv--.

Signed and Sealed this
Eighth Day of August, 2023

Katherine Kelly Vidal
*Director of the United States Patent and Trademark Office*